United States Patent
Petluri et al.

(10) Patent No.: US 11,369,013 B2
(45) Date of Patent: *Jun. 21, 2022

(54) TWO-CHANNEL TUNABLE LIGHTING SYSTEMS WITH CONTROLLABLE EQUIVALENT MELANOPIC LUX AND CORRELATED COLOR TEMPERATURE OUTPUTS

(71) Applicant: EcoSense Lighting, Inc., Los Angeles, CA (US)

(72) Inventors: Raghuram L. V. Petluri, Los Angeles, CA (US); Paul Kenneth Pickard, Los Angeles, CA (US)

(73) Assignee: KORRUS, INC., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/088,242

(22) Filed: Nov. 3, 2020

(65) Prior Publication Data

US 2021/0227657 A1    Jul. 22, 2021

Related U.S. Application Data

(63) Continuation of application No. 16/599,768, filed on Oct. 11, 2019, now Pat. No. 10,827,580, which is a
(Continued)

(51) Int. Cl.
*H05B 45/20* (2020.01)
*F21K 9/00* (2016.01)
(Continued)

(52) U.S. Cl.
CPC ............. *H05B 45/20* (2020.01); *A61M 21/02* (2013.01); *H05B 45/10* (2020.01); *A61M 2021/0044* (2013.01)

(58) Field of Classification Search
CPC ...... H05B 45/10; H05B 45/20; H05B 47/105; F21K 9/00; F21K 9/60; F21K 9/64; F21Y 2113/00; F21Y 2115/00; F21Y 2115/10
See application file for complete search history.

(56) References Cited

U.S. PATENT DOCUMENTS

| 2013/0002157 | A1* | 1/2013 | van de Ven | ............ | H05B 45/46 |
| | | | | | 315/192 |
| 2014/0035472 | A1 | 2/2014 | Raj | | |

(Continued)

FOREIGN PATENT DOCUMENTS

| WO | 2012024243 | 2/2012 |
| WO | 2016130464 | 8/2016 |

(Continued)

OTHER PUBLICATIONS

International Patent Application No. PCT/US2019/060634; Int'l Search Report and the Written Opinion; dated Jan. 27, 2020; 10 pages.
International Search Report dated Apr. 29, 2019, issued in International patent application PCT/US19/13356 filed Jan. 11, 2019, 3 pages.
(Continued)

*Primary Examiner* — Thai Pham
(74) *Attorney, Agent, or Firm* — FisherBroyles LLP

(57) ABSTRACT

The present disclosure provides lighting systems suitable for generating white light. The lighting systems can have a first lighting channel configured to produce a first white light having a first color point and a first spectral power distribution, a second lighting channel configured to produce a second white light having a second color point and a second spectral power distribution, and a control system configured to independently change the intensity of each of the first lighting channel and the second lighting channel. The first lighting channels can have LEDs having an emission with a
(Continued)

first peak wavelength of between about 440 nm and about 510 nm. The second lighting channels can have LEDs having an emission with a second peak wavelength of between about 380 nm and about 420 nm. The disclosure provides methods of generating white light using the lighting systems described.

7 Claims, 15 Drawing Sheets

Related U.S. Application Data continuation of application No. PCT/US2019/013356, filed on Jan. 11, 2019, which is a continuation of application No. PCT/US2018/020792, filed on Mar. 2, 2018.

(60) Provisional application No. 62/757,664, filed on Nov. 8, 2018, provisional application No. 62/712,182, filed on Jul. 30, 2018, provisional application No. 62/712,191, filed on Jul. 30, 2018, provisional application No. 62/634,798, filed on Feb. 23, 2018, provisional application No. 62/616,423, filed on Jan. 11, 2018, provisional application No. 62/616,414, filed on Jan. 11, 2018, provisional application No. 62/616,404, filed on Jan. 11, 2018, provisional application No. 62/616,401, filed on Jan. 11, 2018.

(51) Int. Cl.
*A61M 21/02* (2006.01)
*H05B 45/10* (2020.01)
*A61M 21/00* (2006.01)

(56) References Cited

U.S. PATENT DOCUMENTS

| | | |
|---|---|---|
| 2014/0167601 A1* | 6/2014 | Harry ............... H01L 33/504 313/503 |
| 2014/0312777 A1* | 10/2014 | Shearer ............ H05B 47/105 315/151 |
| 2015/0002034 A1 | 1/2015 | Van De Ven |
| 2015/0062892 A1* | 3/2015 | Krames ............... F21V 29/70 362/231 |
| 2015/0231408 A1 | 8/2015 | Williams |
| 2016/0153622 A1 | 6/2016 | Yu |
| 2016/0153625 A1* | 6/2016 | Maglica ............... F21L 4/045 362/187 |
| 2016/0316527 A1 | 10/2016 | Allen |
| 2017/0219184 A1 | 8/2017 | Petluri |
| 2017/0223786 A1 | 8/2017 | Petluri |
| 2017/0343167 A1 | 11/2017 | Petluri |
| 2017/0354000 A1 | 12/2017 | Gordin |
| 2018/0077767 A1* | 3/2018 | Soler ................. A61N 5/0618 |
| 2018/0160491 A1* | 6/2018 | Biery ................. H05B 45/20 |
| 2019/0254142 A1* | 8/2019 | Petluri ............... G09G 3/3413 |

FOREIGN PATENT DOCUMENTS

| | | |
|---|---|---|
| WO | 2017131715 A1 | 8/2017 |
| WO | 2018130403 | 7/2018 |

OTHER PUBLICATIONS

Written Opinion dated Apr. 29, 2019, issued in International patent application PCT/US19/13356 filed Jan. 11, 2019, 6 pages.
Lucas et al.; "Measuring and using light in the melanopsin age"; Trends in Neurosciences; vol. 37 Issue 1; Jan. 2014; 9 pages.
Ewing et al., "Simulating Circadian Light: Multi-Dimensional Illuminance Analysis", Proceedings of the 15th IBPSA Conference, (Sep. 8, 2017), pp. 2363-2371, URL: http://www.ibpsa.org/proceedings/BS2017/BS2017_660.pdf, XP055624687.

* cited by examiner

TWO-CHANNEL TUNABLE LIGHTING SYSTEMS WITH CONTROLLABLE EQUIVALENT MELANOPIC LUX AND CORRELATED COLOR TEMPERATURE OUTPUTS

CROSS-REFERENCE TO RELATED APPLICATIONS

This application is a continuation of U.S. application Ser. No. 16/599,768, filed Oct. 11, 2019, which is a continuation of International Patent Application No. PCT/US2019/013356, filed Jan. 11, 2019, which claims the benefit of International Application No. PCT/US2018/020792, filed Mar. 2, 2018; U.S. Provisional Patent Application No. 62/616,401 filed Jan. 11, 2018; U.S. Provisional Patent Application No. 62/616,404 filed Jan. 11, 2018; U.S. Provisional Patent Application No. 62/616,414 filed Jan. 11, 2018; U.S. Provisional Patent Application No. 62/616,423 filed Jan. 11, 2018; U.S. Provisional Patent Application No. 62/634,798 filed Feb. 23, 2018; U.S. Provisional Patent Application No. 62/712,191 filed Jul. 30, 2018; U.S. Provisional 62/712,182 filed Jul. 30, 2018; and U.S. Provisional Patent Application No. 62/757,664 filed Nov. 8, 2018, the contents of which are incorporated by reference herein in their entirety as if fully set forth herein.

FIELD OF THE DISCLOSURE

This disclosure is in the field of solid-state lighting. In particular, the disclosure relates to devices for use in, and methods of, providing tunable white light with high color rendering performance and controllable biological effects.

BACKGROUND

A wide variety of light emitting devices are known in the art including, for example, incandescent light bulbs, fluorescent lights, and semiconductor light emitting devices such as light emitting diodes ("LEDs").

There are a variety of resources utilized to describe the light produced from a light emitting device, one commonly used resource is 1931 CIE (Commission Internationale de l'Éclairage) Chromaticity Diagram. The 1931 CIE Chromaticity Diagram maps out the human color perception in terms of two CIE parameters x and y. The spectral colors are distributed around the edge of the outlined space, which includes all of the hues perceived by the human eye. The boundary line represents maximum saturation for the spectral colors, and the interior portion represents less saturated colors including white light. The diagram also depicts the Planckian locus, also referred to as the black body locus (BBL), with correlated color temperatures, which represents the chromaticity coordinates (i.e., color points) that correspond to radiation from a black-body at different temperatures. Illuminants that produce light on or near the BBL can thus be described in terms of their correlated color temperatures (CCT). These illuminants yield pleasing "white light" to human observers, with general illumination typically utilizing CCT values between 1,800K and 10,000K.

Color rendering index (CRI) is described as an indication of the vibrancy of the color of light being produced by a light source. In practical terms, the CRI is a relative measure of the shift in surface color of an object when lit by a particular lamp as compared to a reference light source, typically either a black-body radiator or the daylight spectrum. The higher the CRI value for a particular light source, the better that the light source renders the colors of various objects it is used to illuminate.

Color rendering performance may be characterized via standard metrics known in the art. Fidelity Index (Rf) and the Gamut Index (Rg) can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. In practical terms, the Rf is a relative measure of the shift in surface color of an object when lit by a particular lamp as compared to a reference light source, typically either a black-body radiator or the daylight spectrum. The higher the Rf value for a particular light source, the better that the light source renders the colors of various objects it is used to illuminate. The Gamut Index Rg evaluates how well a light source saturates or desaturates the 99 CES compared to the reference source.

LEDs have the potential to exhibit very high power efficiencies relative to conventional incandescent or fluorescent lights. Most LEDs are substantially monochromatic light sources that appear to emit light having a single color. Thus, the spectral power distribution of the light emitted by most LEDs is tightly centered about a "peak" wavelength, which is the single wavelength where the spectral power distribution or "emission spectrum" of the LED reaches its maximum as detected by a photo-detector. LEDs typically have a full-width half-maximum wavelength range of about 10 nm to 30 nm, comparatively narrow with respect to the broad range of visible light to the human eye, which ranges from approximately from 380 nm to 800 nm.

In order to use LEDs to generate white light, LED lamps have been provided that include two or more LEDs that each emit a light of a different color. The different colors combine to produce a desired intensity and/or color of white light. For example, by simultaneously energizing red, green and blue LEDs, the resulting combined light may appear white, or nearly white, depending on, for example, the relative intensities, peak wavelengths and spectral power distributions of the source red, green and blue LEDs. The aggregate emissions from red, green, and blue LEDs typically provide poor color rendering for general illumination applications due to the gaps in the spectral power distribution in regions remote from the peak wavelengths of the LEDs.

White light may also be produced by utilizing one or more luminescent materials such as phosphors to convert some of the light emitted by one or more LEDs to light of one or more other colors. The combination of the light emitted by the LEDs that is not converted by the luminescent material(s) and the light of other colors that are emitted by the luminescent material(s) may produce a white or near-white light.

LED lamps have been provided that can emit white light with different CCT values within a range. Such lamps utilize two or more LEDs, with or without luminescent materials, with respective drive currents that are increased or decreased to increase or decrease the amount of light emitted by each LED. By controllably altering the power to the various LEDs in the lamp, the overall light emitted can be tuned to different CCT values. The range of CCT values that can be provided with adequate color rendering values and efficiency is limited by the selection of LEDs.

The spectral profiles of light emitted by white artificial lighting can impact circadian physiology, alertness, and cognitive performance levels. Bright artificial light can be used in a number of therapeutic applications, such as in the treatment of seasonal affective disorder (SAD), certain sleep problems, depression, jet lag, sleep disturbances in those with Parkinson's disease, the health consequences associated with shift work, and the resetting of the human circadian clock. Artificial lighting may change natural processes, interfere with melatonin production, or disrupt the circadian rhythm. Blue light may have a greater tendency than other colored light to affect living organisms through the disruption of their biological processes which can rely upon natural cycles of daylight and darkness. Exposure to blue light late in the evening and at night may be detrimental to one's health. Some blue or royal blue light within lower wavelengths can have hazardous effects to human eyes and skin, such as causing damage to the retina.

Significant challenges remain in providing LED lamps that can provide white light across a range of CCT values while simultaneously achieving high efficiencies, high luminous flux, good color rendering, and acceptable color stability. It is also a challenge to provide lighting apparatuses that can provide desirable lighting performance while allowing for the control of circadian energy performance.

DISCLOSURE

The present disclosure provides aspects of lighting systems comprising a first lighting channel configured to produce a first white light having a first color point and a first spectral power distribution, a second lighting channel configured to produce a second white light having a second color point and a second spectral power distribution, and a control system configured to independently change the intensity of each of the first lighting channel and the second lighting channel. In some implementations, the first white light and second white light combined together can form a third white light having a third color point and a third spectral power distribution. In some implementations, the control system can be further configured to change the intensity of each of the first lighting channel and the second lighting channel to provide the third white light with the third color point at a plurality of points along a predefined path near the black body locus in the 1931 CIE Chromaticity Diagram between and including both the first color point and the second color point. In certain implementations, the first spectral power distribution can have a first circadian-stimulating energy characteristic, the second spectral power distribution can have a second circadian-stimulating energy characteristic, and the third spectral power distribution can have a third circadian-stimulating energy characteristic. In some implementations, the third white light at each of the plurality of points along the predefined path can have an Ra value greater than or equal to 80. In some implementations, the first color point can have a CCT between about 4000K and about 6500K. In further implementations, the second color point can have a CCT between about 2700K and about 1800K. The first lighting channels can have LEDs having an emission with a first peak wavelength of between about 440 nm and about 510 nm. The second lighting channels can have LEDs having an emission with a second peak wavelength of between about 380 nm and about 420 nm.

In some aspects, the present disclosure provides methods of generating white light, the methods comprising producing a first white light, a second white light, or a combination of the first white light and the second white light, wherein the first white light is produced from a first lighting channel of a lighting system, the first white light having a first color point and a first spectral power distribution, wherein the second white light is produced from a second lighting channel of the lighting system, the second white light having a second color point and a second spectral power distribution, with the methods further comprising combining the first white light, the second white light, or the combination of the first white light and the second white light to form a third white light having a third color point and a third spectral power distribution, with the methods further comprising changing the intensity of each of the first lighting channel and the second lighting channel with a control system to provide the third white light with the third color point at a plurality of points along a predefined path near the black body locus in the 1931 CIE Chromaticity Diagram between and including both the first color point and the second color point, wherein the first spectral power distribution has a first circadian-stimulating energy characteristic, the second spectral power distribution has a second circadian-stimulating energy characteristic, and the third spectral power distribution has a third circadian-stimulating energy characteristic. In some implementations, the third white light at each of the plurality of points along the predefined path can have an Ra value greater than or equal to 80. In some implementations, the first color point can have a CCT between about 4000K and about 6500K. In some implementations, the second color point can have a CCT between about 2700K and about 1800K. The first lighting channels can have LEDs having an emission with a first peak wavelength of between about 440 nm and about 510 nm. The second lighting channels can have LEDs having an emission with a second peak wavelength of between about 380 nm and about 420 nm.

In some aspects, the present disclosure provides methods of generating white light with the devices described herein.

The general disclosure and the following further disclosure are exemplary and explanatory only and are not restrictive of the disclosure, as defined in the appended claims. Other aspects of the present disclosure will be apparent to those skilled in the art in view of the details as provided herein. In the figures, like reference numerals designate corresponding parts throughout the different views. All callouts and annotations are hereby incorporated by this reference as if fully set forth herein.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale. In the drawings.

Figure 1A:
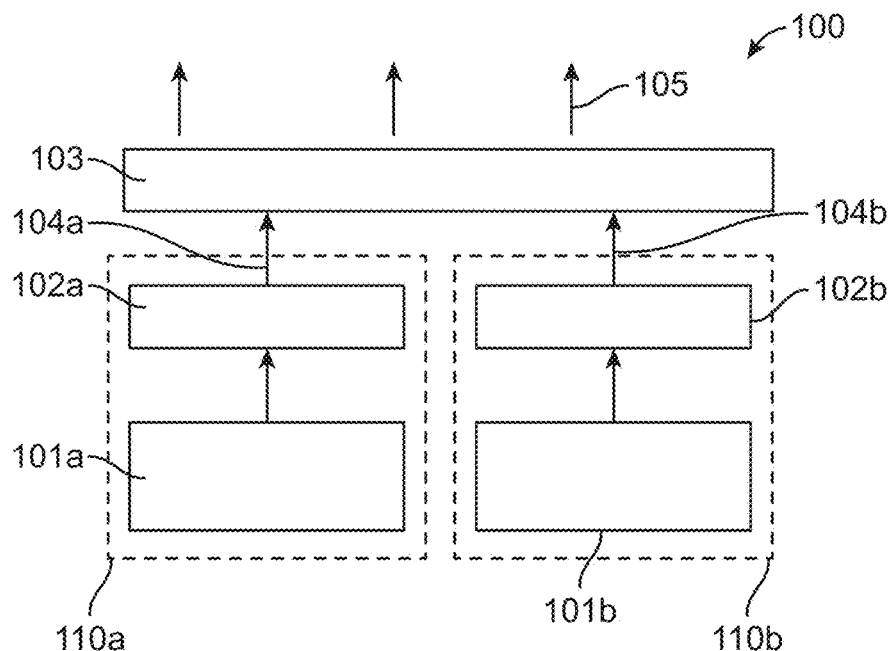
FIG. 1A illustrates aspects of lighting systems according to the present disclosure.

All descriptions and callouts in the Figures are hereby incorporated by this reference as if fully set forth herein.

FURTHER DISCLOSURE

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular exemplars by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another exemplar includes from the one particular value and/or to the other particular value. Similarly, when values are expressed as approximations, by use of the antecedent "about," it will be understood that the particular value forms another exemplar. All ranges are inclusive and combinable.

The term "circadian-stimulating energy characteristics" refers to any characteristics of a spectral power distribution that may have biological effects on a subject. In some aspects, the circadian-stimulating energy characteristics of aspects of the lighting systems of this disclosure can include one or more of CS, CLA, EML, BLH, CER, CAF, LEF, circadian power, circadian flux, and the relative amount of power within one or more particular wavelength ranges.

It is to be appreciated that certain features of the disclosure which are, for clarity, described herein in the context of separate exemplar, may also be provided in combination in a single exemplary implementation. Conversely, various features of the disclosure that are, for brevity, described in the context of a single exemplary implementation, may also be provided separately or in any subcombination. Further, reference to values stated in ranges include each and every value within that range.

In some aspects, the present disclosure provides lighting systems having a first lighting channel and a second lighting channel. The first lighting channels of the present disclosure can be configured to produce a first white light having a first color point and a first spectral power distribution. The second lighting channels of the present disclosure can be configured to produce a second white light having a second color point and a second spectral power distribution. The lighting systems can further include a control system that is configured to independently change the intensity of each of the first and second lighting channels. With different relative intensities of the first and second lighting channels, the lighting system can provide a combined light from combining the first white light and second white light together as a third white light having a third color point and a third spectral power distribution. In some implementations, one of the first and second lighting channels can be shut off completely, such that the third white light is the same as the other of the first and second lighting channels that is not shut off; in further implementations, the other channel can be shut off such that the third white light is the same as the other lighting channel. In some implementations the third white light can be switched from being the same as the first lighting channel and the same as the second lighting channel by alternately shutting off and turning on the first and second lighting channels. In further implementations, a plurality of third color points can be generated along the tie line between a particular pair of first color point and second color point of the first and second lighting channels on the 1931 CIE Chromaticity Diagram. In some implementations, the plurality of third color points can form a predefined path near the black body locus on the 1931 CIE Chromaticity Diagram. In certain implementations, the plurality of third color points can form a predefined path within a 7-step MacAdam ellipse around any point on the black body locus having a CCT between the CCT of the first color point and the CCT of the second color point. In further implementations, lighting systems can output third white light at third color points along a predetermined path shifted −7±2 DUV from the black body locus having a correlated color temperature between the CCT of the first color point and the CCT of the second color point.

Figure 5:
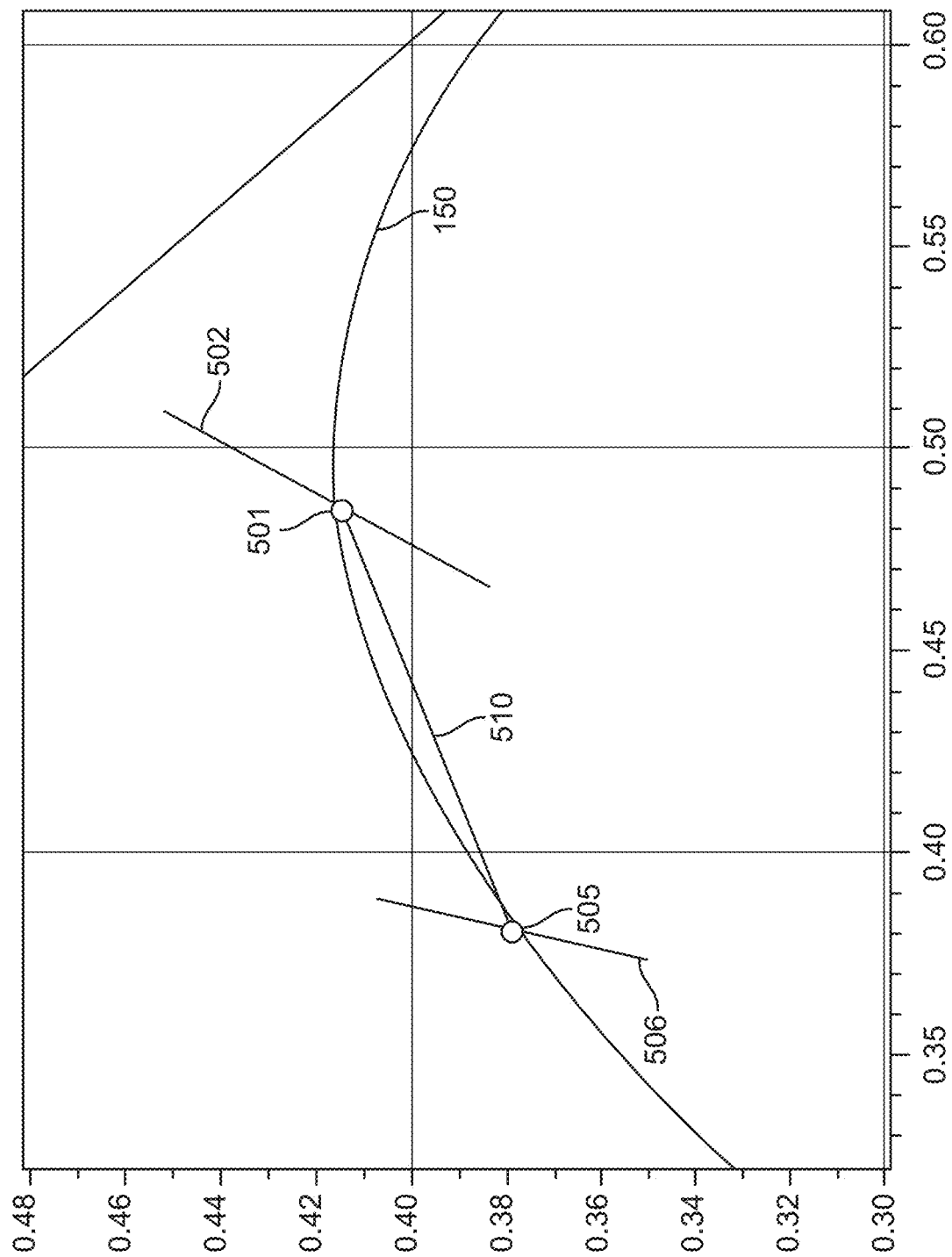
FIG. 5 illustrates some aspects of lighting systems according to the present disclosure.

FIG. 5 schematically shows aspects of implementations of lighting systems of the present disclosure. A first color point 505 and a second color points 501 are shown, along with respective constant CCT lines 506 and 502 for reference. As depicted, the first color point 505 has a CCT value of approximately 4000K, but in other implementations may have other CCT values as described elsewhere herein. As depicted, the second color point 501 has a CCT value of approximately 2400K, but in other implementations may have other CCT values as described elsewhere herein. The first and second color points 505/501 are depicted relative to the black body locus 150 in a portion of the 1931 CIE Chromaticity Diagram. In some implementations, at least a portion of the tie line 510 between the first color point 505 and second color point 501 can form a predefined path of a plurality of third color points generated by the lighting system.

Figure 6:
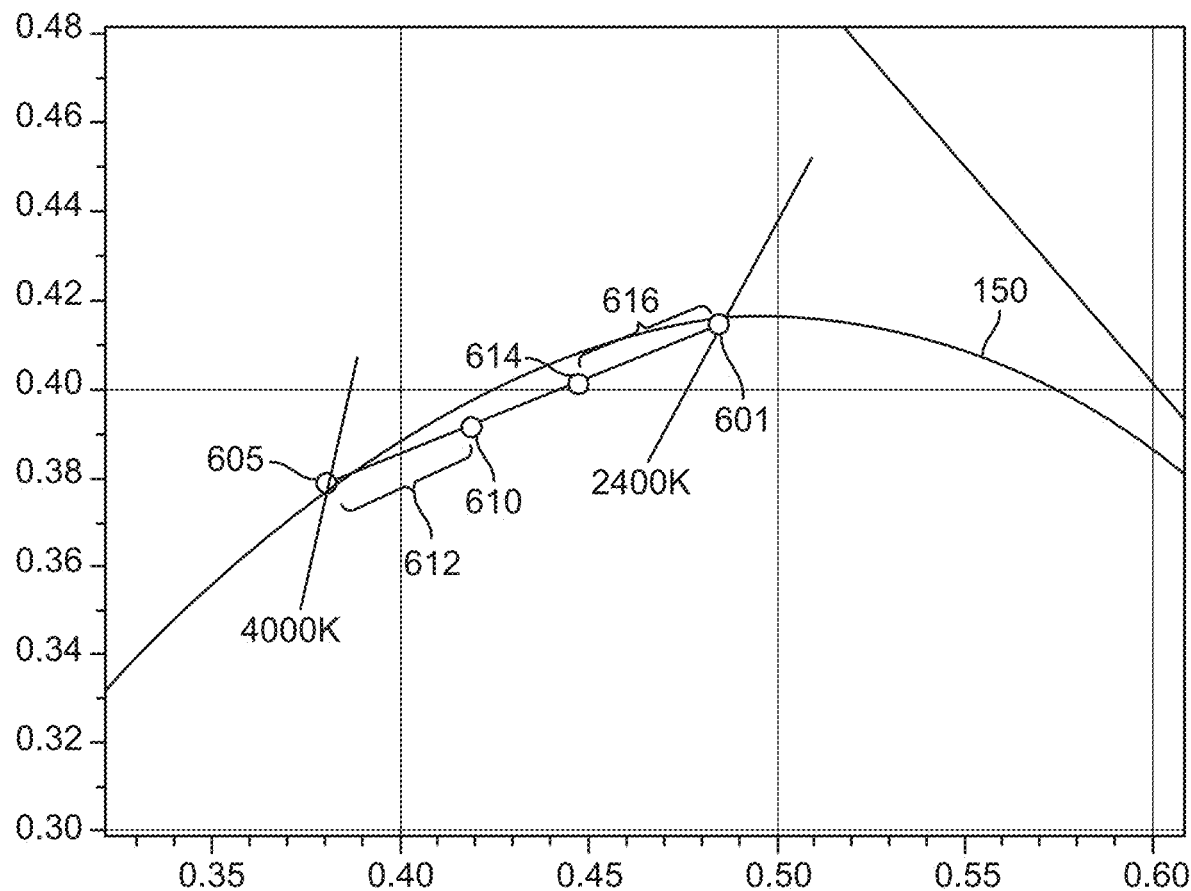
FIG. 6 illustrates some aspects of lighting systems according to the present disclosure.

FIG. 6 schematically shows aspects of implementations of lighting systems of the present disclosure. A first color point 605 and a second color point 601 are shown, along with respective constant CCT lines labeled with the approximate respective CCT values 4000K and 2400K of the first and second color points 605/601 for reference. As depicted, the first color point 605 has a CCT value of approximately 4000K, but in other implementations may have other CCT values as described elsewhere herein. As depicted, the second color point 601 has a CCT value of approximately 2400K, but in other implementations may have other CCT values as described elsewhere herein. The first and second color points 605/601 are depicted relative to the black body locus 150 in a portion of the 1931 CIE Chromaticity Diagram. A tie line between the first color point 605 and second color point 601 can form a predefined path of a plurality of third color points generated by the lighting system. In some implementations, a first threshold point 610 can lie on the tie line and have a first threshold CCT value. In further implementations, a second threshold point 614 can lie on the tie line and have a second threshold CCT value. The third color point can have particular characteristics for points in a region 612 on the tie line between the first color point 605 and the first threshold point 610. The third color point can have particular characteristics for points in a region 616 on the tie line between the second color point 601 and the second threshold point 614.

Figure 8:
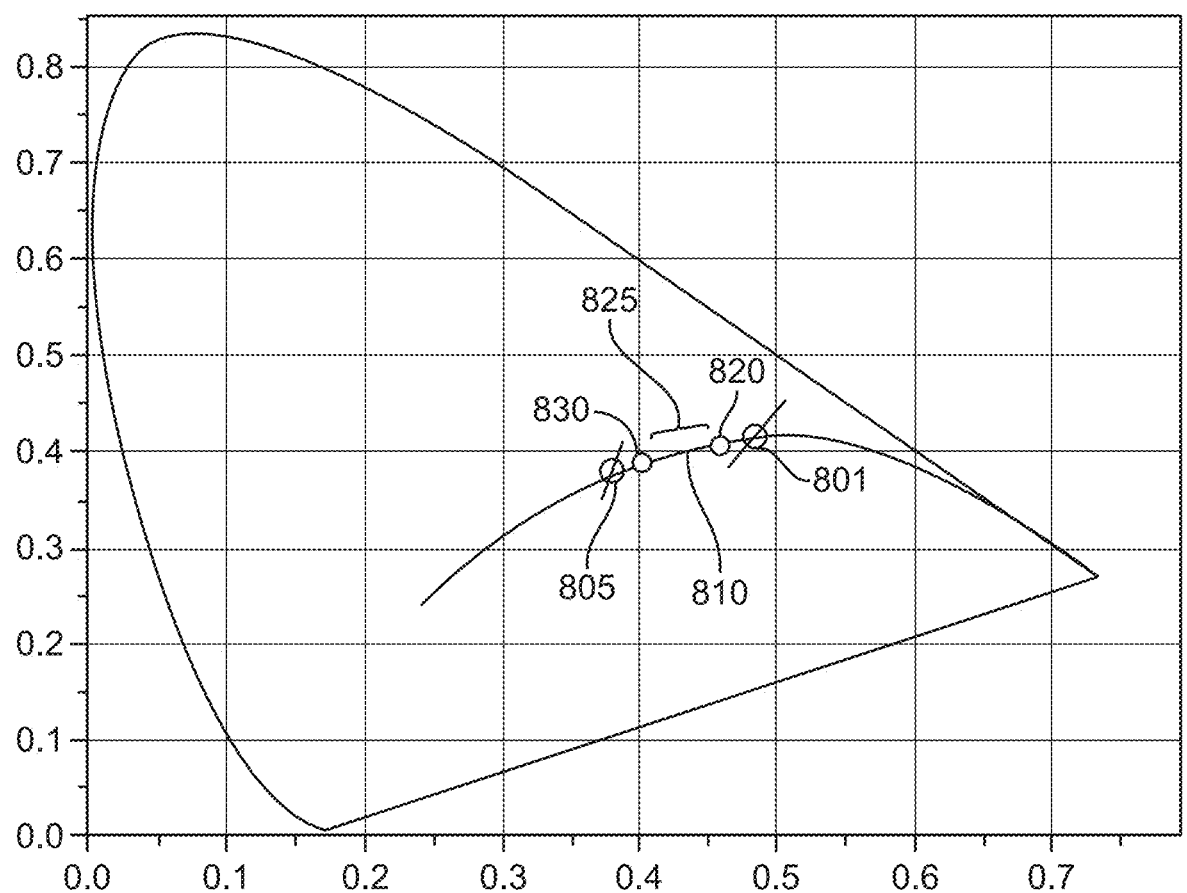
FIG. 8 illustrates some aspects of lighting systems according to the present disclosure.

FIG. 8 schematically shows aspects of implementations of lighting systems of the present disclosure. A first color point 805 and a second color point 801 are shown, along with respective constant CCT lines labeled with the approximate respective CCT values 4000K and 2400K of the first and second color points 805/801 for reference. As depicted, the first color point 805 has a CCT value of approximately 4000K, but in other implementations may have other CCT values as described elsewhere herein. As depicted, the second color point 801 has a CCT value of approximately 2400K, but in other implementations may have other CCT values as described elsewhere herein. The first and second color points 805/801 are depicted relative to the black body locus 150 in a portion of the 1931 CIE Chromaticity Diagram. A tie line 810 between the first color point 805 and second color point 801 can form a predefined path of a plurality of third color points generated by the lighting system. In some implementations, a first threshold point 830 can lie on the tie line and have a first threshold CCT value. In further implementations, a second threshold point 820 can lie on the tie line and have a second threshold CCT value. The third color point can have particular characteristics for points in a region 825 on the tie line between the first threshold point 830 and the second threshold point 820. The third color point can have particular characteristics for points in a region on the tie line between the first color point 805 and the first threshold point 830. The third color point can have particular characteristics for points in a region on the tie line between the second color point 801 and the second threshold point 820.

Figure 1B:
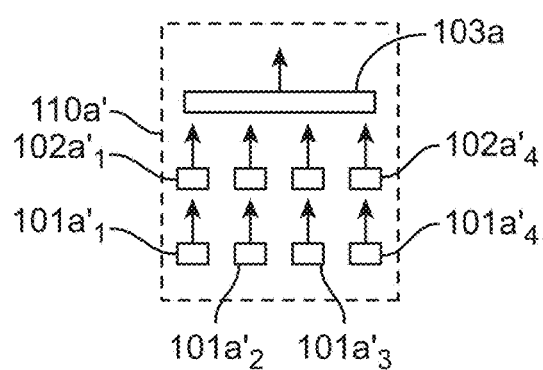
FIG. 1B illustrates aspects of lighting systems according to the present disclosure.
Figure 1C:
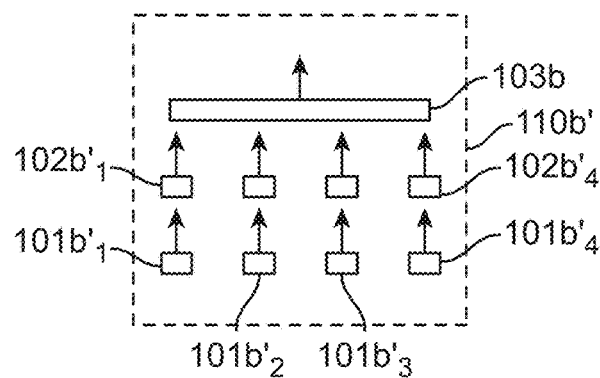
FIG. 1C illustrates aspects of lighting systems according to the present disclosure.

In some implementations, the first and second lighting channels are each provided as one or more LEDs that emit saturated light that excites one or more luminescent materials in a luminophoric medium. FIG. 1 schematically depicts aspects of lighting systems of the present disclosure. An exemplary lighting system 100 is depicted schematically with first and second lighting channels. A first lighting channel 110A having a first LED 101A and a first luminophoric medium 102A together can emit a first white light 104A having a first color point and a first spectral power distribution. The combination of the first LED 101A and the first luminophoric medium 102A together form the first lighting channel. First lighting channels of the present disclosure can comprise a single pair of an LED and a luminophoric medium, as depicted schematically in FIG. 1, or alternatively can comprise a plurality of pairs of LEDs and associated luminophoric mediums in an LED string. FIG. 1B schematically depicts alternative implementations of first lighting channel 110A' formed from a plurality of LEDs 101A'$_1$, 101A'$_2$, 101A'$_3$, and 101A'$_4$, that are each associated with a respective luminophoric medium 102A'$_1$, 102A'$_2$, 102A'$_3$, and 102A'$_4$, which can optionally have the emitted light mixed together by an optional first-lighting-channel optical element 103A. A second lighting channel having a first LED 101B and a second luminophoric medium 102B together can emit a second white light 104B having a second color point and a second spectral power distribution. The combination of the second LED 101B and the second luminophoric medium 102B together form the second lighting channel. Second lighting channels of the present disclosure can comprise a single pair of an LED and a luminophoric medium, as depicted schematically in FIG. 1, or alternatively can comprise a plurality of pairs of LEDs and associated luminophoric mediums in an LED string. FIG. 1C schematically depicts alternative implementations of second lighting channel 110B' formed from a plurality of LEDs 101B'$_1$, 101B'$_2$, 101B'$_3$, and 101B'$_4$, that are each associated with a respective luminophoric medium 102B'$_1$, 102B'$_2$, 102B'$_3$, and 102B'$_4$, which can optionally have the emitted light mixed together by an optional second-lighting-channel optical element 103B. The first white light 104A and the second white light 104B can be combined together to form a third white light 105. The first and second white lights 104A/104B can be passed through one or more optical elements 103 in order to mix, combine, or shape the light output from the lighting system as desired.

The recipient luminophoric mediums 102A, 102B, 102A'$_1$, 102A'$_2$, 102A'$_3$, 102A'$_4$, 102B'$_1$, 102B'$_2$, 102B'$_3$, and 102B'$_4$ can includes one or more luminescent materials and can be positioned to receive light that is emitted by an LED or other semiconductor light emitting device. In some implementations, recipient luminophoric mediums include layers having luminescent materials that are coated or sprayed directly onto a semiconductor light emitting device or on surfaces of the packaging thereof, and clear encapsulants that include luminescent materials that are arranged to partially or fully cover a semiconductor light emitting device. A recipient luminophoric medium may include one medium layer or the like in which one or more luminescent materials are mixed, multiple stacked layers or mediums, each of which may include one or more of the same or different luminescent materials, and/or multiple spaced apart layers or mediums, each of which may include the same or different luminescent materials. Suitable encapsulants are known by those skilled in the art and have suitable optical, mechanical, chemical, and thermal characteristics. In some implementations, encapsulants can include dimethyl silicone, phenyl silicone, epoxies, acrylics, and polycarbonates. In some implementations, a recipient luminophoric medium can be spatially separated (i.e., remotely located) from an LED or surfaces of the packaging thereof. In some implementations, such spatial segregation may involve separation of a distance of at least about 1 mm, at least about 2 mm, at least about 5 mm, or at least about 10 mm. In certain embodiments, conductive thermal communication between a spatially segregated luminophoric medium and one or more electrically activated emitters is not substantial. Luminescent materials can include phosphors, scintillators, day glow tapes, nanophosphors, inks that glow in visible spectrum upon illumination with light, semiconductor quantum dots, or combinations thereof. In some implementations, the luminescent materials may comprise phosphors comprising one or more of the following materials: $BaMg_2Al_{16}O_{27}$:$Eu^{2+}$, $BaMg_2Al_{16}O_{27}$:$Eu^{2+}$,$Mn^{2+}$, $CaSiO_3$:Pb,Mn, $CaWO_4$:Pb, $MgWO_4$, $Sr_5Cl(PO_4)_3$:$Eu^{2+}$, $Sr_2P_2O_7$:$Sn^{2+}$, $Sr_6P_5BO_{20}$:Eu, $Ca_5F(PO_4)_3$:Sb, $(Ba,Ti)_2P_2O_7$:Ti, $Sr_5F(PO_4)_3$:Sb,Mn, (La,Ce,Tb)$PO_4$:Ce,Tb, $(Ca,Zn,Mg)_3(PO_4)_2$:Sn, $(Sr,Mg)_3(PO_4)_2$:Sn, $Y_2O_3$:$Eu^{3+}$, $Mg_4(F)GeO_6$:Mn, $LaMgAl_{11}O_{19}$:Ce, $LaPO_4$:Ce, $SrAl_{12}O_{19}$:Ce, $BaSi_2O_5$:Pb, $SrB_4O_7$:Eu, $Sr_2MgSi_2O_7$:Pb, $Gd_2O_2S$:Tb, $Gd_2O_2S$:Eu, $Gd_2O_2S$:Pr, $Gd_2O_2S$:Pr,Ce,F, $Y_2O_2S$:Tb, $Y_2O_2S$:Eu, $Y_2O_2S$:Pr, Zn(0.5)Cd(0.4)S:Ag, Zn(0.4)Cd(0.6)S:Ag, $Y_2SiO_5$:Ce, $YAlO_3$:Ce, $Y_3(Al,Ga)_5O_{12}$:Ce, CdS:In, ZnO:Ga, ZnO:Zn, (Zn,Cd)S:Cu,Al, ZnCdS:Ag,Cu, ZnS:Ag, ZnS:Cu, NaI:Tl, CsI:Tl, $^6$LiF/ZnS:Ag, $^6$LiF/ZnS:Cu,Al,Au, ZnS:Cu,Al, ZnS:Cu,Au,Al, $CaAlSiN_3$:Eu, $(Sr,Ca)Al SiN_3$:Eu, $(Ba,Ca,Sr,Mg)_2SiO_4$:Eu, $Lu_3Al_5O_{12}$:Ce, $EU^{3+}(Gd_{0.9}Y_{0.1})_3Al_5O_{12}$:$Bi^{3+},Tb^{3+}$, $Y_3Al_5O_{12}$:Ce, $(La,Y)_3Si_6N_{11}$:Ce, $Ca_2AlSi_3O_2N_5$:$Ce^{3+}$, $Ca_2AlSi_3O_2N_5$:$Eu^{2+}$, $BaMgAl_{10}O_{17}$:Eu, $Sr_5(PO_4)_3Cl$:Eu, $(Ba,Ca,Sr,Mg)_2SiO_4$:Eu, $Si_{6-z}Al_zN_{8-z}O_z$:Eu (wherein $0 < z \le 4.2$); $M_3Si_6O_{12}N_2$:Eu (wherein M=alkaline earth metal element), $(Mg,Ca,Sr,Ba)Si_2O_2N_2$:Eu, $Sr_4Al_{14}O_{25}$:Eu, $(Ba,Sr,Ca)Al_2O_4$:Eu, $(Sr,Ba)Al_2Si_2O_8$:Eu, $(Ba,Mg)_2SiO_4$:Eu, $(Ba,Sr,Ca)_2(Mg, Zn)Si_2O_7$:Eu, $(Ba,Ca,Sr,Mg)_9(Sc,Y,Lu,Gd)_2(Si,Ge)_6O_{24}$:Eu, $Y_2SiO_5$:CeTb, $Sr_2P_2O_7$—$Sr_2B_2O_5$:Eu, $Sr_2Si_3O_8$-$2SrCl_2$:Eu, $Zn_2SiO_4$:Mn, $CeMgAl_{11}O_{19}$:Tb, $Y_3Al_5O_{12}$:Tb, $Ca_2Y_8(SiO_4)_6O_2$:Tb, $La_3Ga_5SiO_{14}$:Tb, $(Sr,Ba,Ca)Ga_2S_4$:Eu,Tb,Sm, $Y_3(Al_1,Ga)_5O_{12}$:Ce, $(Y,Ga,Tb,La,Sm,Pr,Lu)_3(Al,Ga)_5O_{12}$:Ce, $Ca_3Sc_2Si_3O_{12}$:Ce, $Ca_3(Sc,Mg,Na,Li)_2Si_3O_{12}$:Ce, $CaSc_2O_4$:Ce, Eu-activated $SrA_{12}O_4$:Eu, $(La,Gd,Y)_2O_2S$:Tb, $CeLaPO_4$:Tb, ZnS:Cu,Al, ZnS:Cu,Au,Al, $(Y,Ga,Lu,Sc,La)BO_3$:Ce,Tb, $Na_2Gd_2B_2O_7$:Ce,Tb, $(Ba,Sr)_2(Ca,Mg,Zn)B_2O_6$:K,Ce,Tb, $Ca_8Mg(SiO_4)_4Cl_2$:Eu,Mn, $(Sr,Ca,Ba)(Al,Ga,In)_2S_4$:Eu, $(Ca,Sr)_8(Mg,Zn)(SiO_4)_4Cl_2$:Eu,Mn, $M_3Si_6O_9N_4$:Eu, $Sr_5Al_5Si_{21}O_2N_{35}$:Eu, $Sr_3Si_{13}Al_3N_{21}O_2$:Eu, $(Mg,Ca,Sr,Ba)_2Si_5N_8$:Eu, $(La,Y)_2O_2S$:Eu, $(Y,La,Gd,Lu)_2O_2S$:Eu, $Y(V,P)O_4$:Eu, $(Ba,Mg)_2SiO_4$:Eu,Mn, $(Ba,Sr, Ca,Mg)_2SiO_4$:Eu,Mn, $LiW_2O_8$:Eu, $LiW_2O_8$:Eu,Sm, $Eu_2W_2O_9$, $Eu_2W_2O_9$:Nb and $Eu_2W_2O_9$:Sm, (Ca,Sr)S:Eu, $YA_1O_3$:Eu, $Ca_2Y_8(SiO_4)_6O_2$:Eu, $LiY_9(SiO_4)_6O_2$:Eu, $(Y,Gd)_3A_{15}O_{12}$:Ce, $(Tb,Gd)_3A_{15}O_{12}$:Ce, $(Mg,Ca,Sr,Ba)_2Si_5(N,O)_8$:Eu, $(Mg,Ca,Sr,Ba)Si(N,O)_2$:Eu, $(Mg,Ca,Sr,Ba)AlSi(N,O)_3$:Eu, $(Sr,Ca,Ba,Mg)_{10}(PO_4)_6Cl_2$:Eu, Mn, $Eu,Ba_3MgSi_2O_8$:Eu,Mn, $(Ba,Sr,Ca,Mg)_3(Zn,Mg)Si_2O_8$:Eu,Mn, $(k-x)MgO.xAF_2.GeO_2$:$yMn^{4+}$ (wherein k=2.8 to 5, x=0.1 to 0.7, y=0.005 to 0.015, A=Ca, Sr, Ba, Zn or a mixture thereof), Eu-activated α-Sialon, $(Gd,Y,Lu,La)_2O_3$:Eu, Bi, $(Gd,Y,Lu,La)_2O_2S$:Eu,Bi, $(Gd,Y, Lu,La)VO_4$:Eu,Bi, $SrY_2S_4$:Eu,Ce, $CaLa_2S_4$:Ce,Eu, $(Ba,Sr,Ca)MgP_2O_7$:Eu, Mn, $(Sr,Ca,Ba,Mg,Zn)_2P_2O_7$:Eu, Mn, $(Y,Lu)_2WO_6$:Eu,Ma, $(Ba,Sr,Ca)xSiyNz$:Eu,Ce (wherein x, y and z are integers equal to or greater than 1),$(Ca,Sr,Ba,Mg)_{10}(PO_4)_6(F,Cl,Br,OH)$:Eu,Mn, $((Y,Lu,Gd,Tb)_{1-x-y}Sc_xCe_y)_2(Ca,Mg)(Mg,Zn)_{2+r}Si_{z-g}Ge_qO_{12+\delta}$, $SrAlSi_4N_7$, $Sr_2Al_2Si_9O_2N_{14}$:Eu, $M^1{}_aM^2{}_bM^3{}_cO_d$ (wherein $M^1$=activator element including at least Ce, $M^2$=bivalent metal element, $M^3$=trivalent metal element, $0.0001 \le a \le 0.2$, $0.8 \le b \le 1.2$, $1.6 \le c \le 2.4$ and $3.2 \le d \le 4.8$), $A_{2+x}M_yMn_zF_n$ (wherein A=Na and/or K; M=Si and Al, and $-1 \le x \le 1$, $0.9 \le y+z \le 1.1$, $0.001 \le z \le 0.4$ and $5 \le n \le 7$), KSF/KSNAF, or $(La_{1-x-y}, Eu_x, Ln_y)_2O_2S$ (wherein $0.02 \le x \le 0.50$ and $0 \le y \le 0.50$, $Ln = Y^{3+}$, $Gd^{3+}$, $Lu^{3+}$, $Sc^{3+}$, $Sm^{3+}$ or $Er^{3+}$). In some preferred implementations, the luminescent materials may comprise phosphors comprising one or more of the following materials: $CaAlSiN_3$:Eu, $(Sr,Ca)AlSiN_3$:Eu, $BaMgAl_{10}O_{17}$:Eu, $(Ba,Ca,Sr,Mg)_2SiO_4$:Eu, β-SiAlON, $Lu_3A_{15}O_{12}$:Ce, $Eu^{3+}(Cd_{0.9}Y_{0.1})_3A_{15}O_{12}$:$Bi^{3+},Tb^{3+}$, $Y_3A_{15}O_{12}$:Ce, $La_3Si_6N_{11}$:Ce, $(La,Y)_3Si_6N_{11}$:Ce, $Ca_2AlSi_3O_2N_5$:$Ce^{3+}$, $Ca_2AlSi_3O_2N_5$:$Ce^{3+},Eu^{2+}$, $Ca_2AlSi_3O_2N_5$:$Eu^{2+}$, $BaMgAl_{10}O_{17}$:$Eu^{2+}$, $Sr_{4.5}Eu_{0.5}$-$(PO_4)_3Cl$, or $M^1{}_aM^2{}_bM^3{}_cO_d$ (wherein $M^1$=activator element comprising Ce, $M^2$=bivalent metal element, $M^3$=trivalent metal element, $0.0001 \le a \le 0.2$, $0.8 \le b \le 1.2$, $1.6 \le c \le 2.4$ and $3.2 \le d \le 4.8$). In further preferred implementations, the luminescent materials may comprise phosphors comprising one or more of the following materials: $CaAlSiN_3$:Eu, $BaMgAl_{10}O_{17}$:Eu, $Lu_3A_{15}O_{12}$:Ce, or $Y_3A_{15}O_{12}$:Ce.

Figure 2:
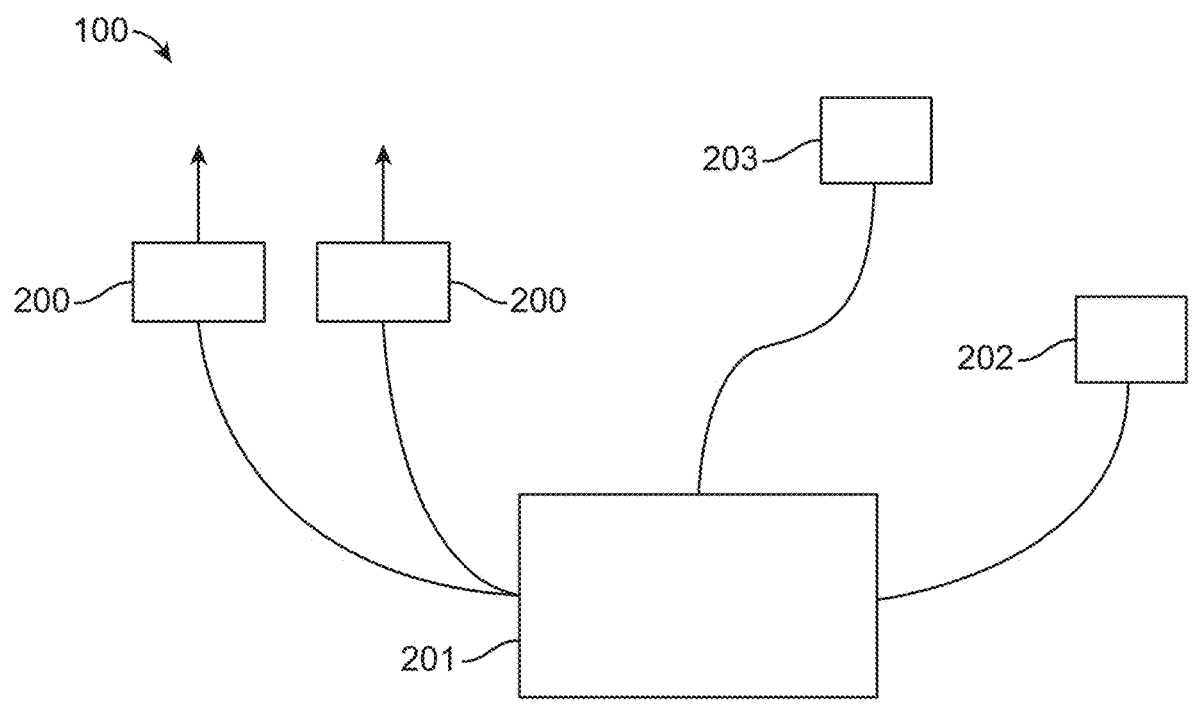
FIG. 2 illustrates aspects of lighting systems according to the present disclosure.

Some implementations of the present invention relate to use of LEDs incorporated into solid state emitter packages. A solid state emitter package typically includes at least one solid state emitter chip that is enclosed with packaging elements to provide environmental and/or mechanical protection, color selection, and light focusing, as well as electrical leads, contacts or traces enabling electrical connection to an external circuit. Encapsulant material, optionally including luminophoric material, may be disposed over solid state emitters in a solid state emitter package. Multiple solid state emitters may be provided in a single package. A package including multiple solid state emitters may include at least one of the following: a single leadframe arranged to conduct power to the solid state emitters, a single reflector arranged to reflect at least a portion of light emanating from each solid state emitter, a single submount supporting each solid state emitter, and a single lens arranged to transmit at least a portion of light emanating from each solid state emitter. Individual LEDs or groups of LEDs in a solid state package (e.g., wired in series) may be separately controlled. As depicted schematically in FIG. 2, multiple solid state emitter packages 200 may be arranged in a single semiconductor light emitting device 100. First and second light channels of the disclosure may be provided in solid state emitter packages 200. Individual solid state emitter packages or groups of solid state emitter packages (e.g., wired in series) may be separately controlled. Separate control of individual emitters, groups of emitters, individual packages, or groups of packages, may be provided by independently applying drive currents to the relevant components with control elements known to those skilled in the art. In one embodiment, at least one control circuit 201 a may include a current supply circuit configured to independently apply an on-state drive current to each individual solid state emitter, group of solid state emitters, individual solid state emitter package, or group of solid state emitter packages. Such control may be responsive to a control signal (optionally including at least one sensor 202 arranged to sense electrical, optical, and/or thermal properties and/or environmental conditions), and a control system 203 may be configured to selectively provide one or more control signals to the at least one current supply circuit. The design and fabrication of semiconductor light emitting devices are well known to those skilled in the art, and hence further description thereof will be omitted. In various embodiments, current to different circuits or circuit portions may be pre-set, user-defined, or responsive to one or more inputs or other control parameters. The lighting systems can be controlled via methods described in U.S. Provisional Patent Application Ser. No. 62/491,137, filed Apr. 27, 2017, entitled Methods and Systems for An Automated Design, Fulfillment, Deployment and Operation Platform for Lighting Installations, U.S. Provisional Patent Application Ser. No. 62/562,714, filed Sep. 25, 2017, entitled Methods and Systems for An Automated Design, Fulfillment, Deployment and Operation Platform for Lighting Installations, and International Patent Application No. PCT/US2018/029380, filed Apr. 25, 2018 and entitled Methods and Systems for an Automated Design, Fulfillment, Deployment and Operation Platform for Lighting Installations, published as International Publication No. WO 2018/200685 A2, each of which hereby are incorporated by reference as if fully set forth herein in their entirety.

Figure 3:
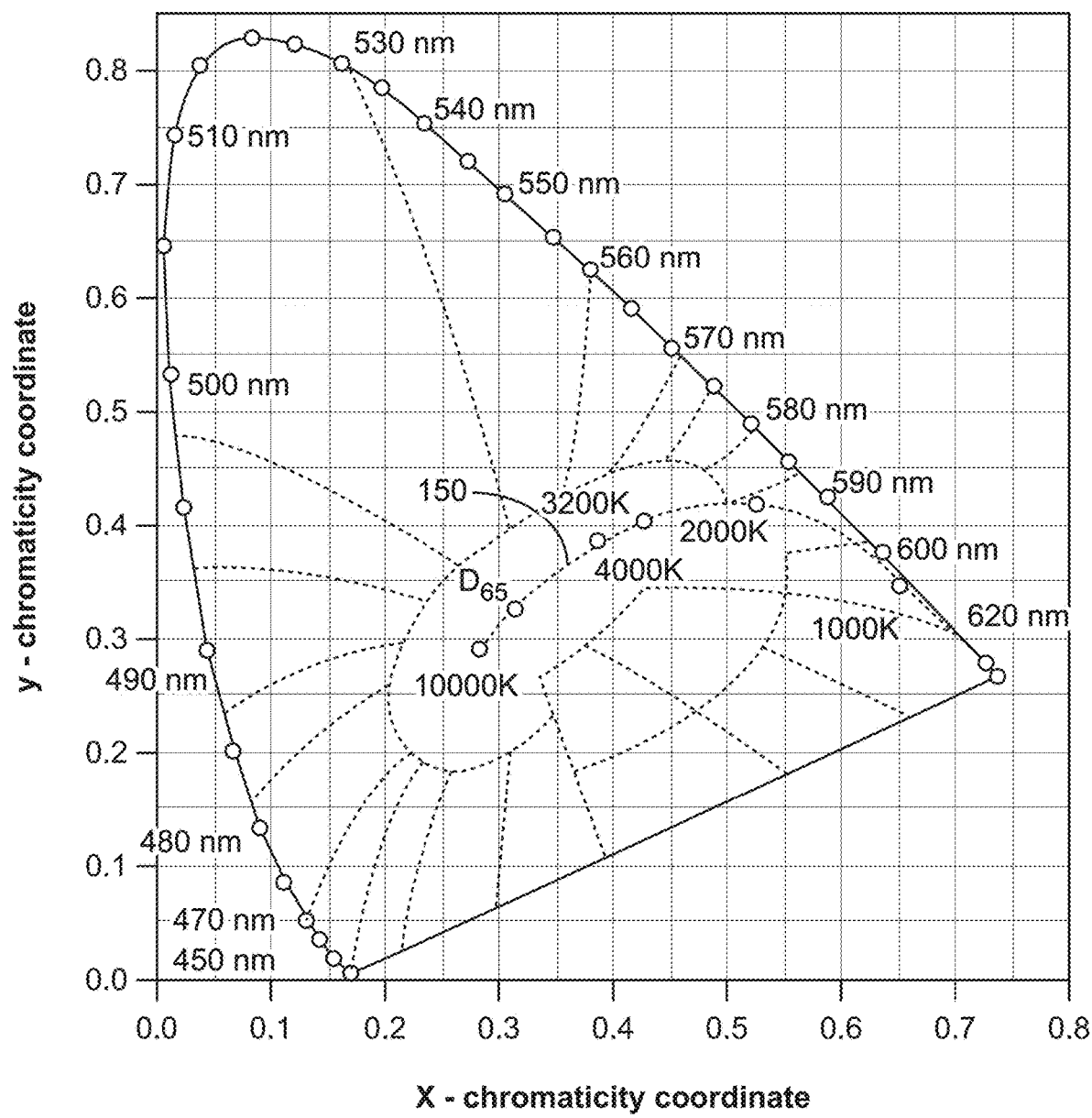
FIG. 3 depicts a graph of a 1931 CIE Chromaticity Diagram illustrating the location of the Planckian locus.

FIG. 3 illustrates a 1931 International Commission on Illumination (CIE) chromaticity diagram. The 1931 CIE Chromaticity diagram is a two-dimensional chromaticity space in which every visible color is represented by a point having x- and y-coordinates, also referred to herein as (ccx, ccy) coordinates. Fully saturated (monochromatic) colors appear on the outer edge of the diagram, while less saturated colors (which represent a combination of wavelengths) appear on the interior of the diagram. The term "saturated", as used herein, means having a purity of at least 85%, the term "purity" having a well-known meaning to persons skilled in the art, and procedures for calculating purity being well-known to those of skill in the art. The Planckian locus 150, or black body locus (BBL), represented by line 150 on the diagram, follows the color an incandescent black body would take in the chromaticity space as the temperature of the black body changes from about 1000K to 10,000 K. The black body locus goes from deep red at low temperatures (about 1000 K) through orange, yellowish white, white, and finally bluish white at very high temperatures. The temperature of a black body radiator corresponding to a particular color in a chromaticity space is referred to as the "correlated color temperature." In general, light corresponding to a correlated color temperature (CCT) of about 2700 K to about 6500 K is considered to be "white" light. In particular, as used herein, "white light" generally refers to light having a chromaticity point that is within a 10-step MacAdam ellipse of a point on the black body locus having a CCT between 2700K and 6500K. However, it will be understood that tighter or looser definitions of white light can be used if desired. For example, white light can refer to light having a chromaticity point that is within a seven step MacAdam ellipse of a point on the black body locus having a CCT between 2700K and 6500K. The distance from the black body locus can be measured in the CIE 1960 chromaticity diagram, and is indicated by the symbol $\Delta uv$, or DUV or duv as referred to elsewhere herein. If the chromaticity point is above the Planckian locus the DUV is denoted by a positive number; if the chromaticity point is below the locus, DUV is indicated with a negative number. If the DUV is sufficiently positive, the light source may appear greenish or yellowish at the same CCT. If the DUV is sufficiently negative, the light source can appear to be purple or pinkish at the same CCT. Observers may prefer light above or below the Planckian locus for particular CCT values. DUV calculation methods are well known by those of ordinary skill in the art and are more fully described in ANSI C78.377, American National Standard for Electric Lamps—Specifications for the Chromaticity of Solid State Lighting (SSL) Products, which is incorporated by reference herein in its entirety for all purposes. A point representing the CIE Standard Illuminant D65 is also shown on the diagram. The D65 illuminant is intended to represent average daylight and has a CCT of approximately 6500K and the spectral power distribution is described more fully in Joint ISO/CIE Standard, ISO 10526:1999/CIE 5005/E-1998, CIE Standard Illuminants for Colorimetry, which is incorporated by reference herein in its entirety for all purposes.

The color points described in the present disclosure can be within color-point ranges defined by geometric shapes on the 1931 CIE Chromaticity Diagram that enclose a defined set of ccx, ccy color coordinates. It should be understood that any gaps or openings in any described or depicted boundaries for color-point ranges should be closed with straight lines to connect adjacent endpoints in order to define a closed boundary for each color-point range.

The light emitted by a light source may be represented by a point on a chromaticity diagram, such as the 1931 CIE chromaticity diagram, having color coordinates denoted (ccx, ccy) on the X-Y axes of the diagram. A region on a chromaticity diagram may represent light sources having similar chromaticity coordinates.

The ability of a light source to accurately reproduce color in illuminated objects can be characterized using the color rendering index ("CRI"), also referred to as the CIE Ra value. The Ra value of a light source is a modified average of the relative measurements of how the color rendition of an illumination system compares to that of a reference black-body radiator or daylight spectrum when illuminating eight reference colors R1-R8. Thus, the Ra value is a relative measure of the shift in surface color of an object when lit by a particular lamp. The Ra value equals 100 if the color coordinates of a set of test colors being illuminated by the illumination system are the same as the coordinates of the same test colors being irradiated by a reference light source of equivalent CCT. For CCTs less than 5000K, the reference illuminants used in the CRI calculation procedure are the SPDs of blackbody radiators; for CCTs above 5000K, imaginary SPDs calculated from a mathematical model of daylight are used. These reference sources were selected to approximate incandescent lamps and daylight, respectively. Daylight generally has an Ra value of nearly 100, incandescent bulbs have an Ra value of about 95, fluorescent lighting typically has an Ra value of about 70 to 85, while monochromatic light sources have an Ra value of essentially zero. Light sources for general illumination applications with an Ra value of less than 50 are generally considered very poor and are typically only used in applications where economic issues preclude other alternatives. The calculation of CIE Ra values is described more fully in Commission Internationale de l'Éclairage. 1995. *Technical Report: Method of Measuring and Specifying Colour Rendering Properties of Light Sources*, CIE No. 13.3-1995. Vienna, Austria: Commission Internationale de l'Éclairage, which is incorporated by reference herein in its entirety for all purposes. In addition to the Ra value, a light source can also be evaluated based on a measure of its ability to render a saturated red reference color R9, also known as test color sample 9 ("TCS09"), with the R9 color rendering value ("R9 value"). Light sources can also be evaluated based on a measure of ability to render additional colors R10-R15, which include realistic colors like yellow, green, blue, Caucasian skin color (R13), tree leaf green, and Asian skin color (R15), respectively. Light sources can further be evaluated by calculating the gamut area index ("GAI"). Connecting the rendered color points from the determination of the CIE Ra value in two dimensional space will form a gamut area. Gamut area index is calculated by dividing the gamut area formed by the light source with the gamut area formed by a reference source using the same set of colors that are used for CRI. GAI uses an Equal Energy Spectrum as the reference source rather than a black body radiator. A gamut area index related to a black body radiator ("GAIBB") can be calculated by using the gamut area formed by the blackbody radiator at the equivalent CCT to the light source.

The ability of a light source to accurately reproduce color in illuminated objects can be characterized using the metrics described in *IES Method for Evaluating Light Source Color Rendition*, Illuminating Engineering Society, Product ID: TM-30-15 (referred to herein as the "TM-30-15 standard"), which is incorporated by reference herein in its entirety for all purposes. The TM-30-15 standard describes metrics including the Fidelity Index (Rf) and the Gamut Index (Rg) that can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. Rg values provide a measure of the color gamut that the light source provides relative to a reference illuminant. The range of Rg depends upon the Rf value of the light source being tested. The reference illuminant is selected depending on the CCT. For CCT values less than or equal to 4500K, Planckian radiation is used. For CCT values greater than or equal to 5500K, CIE Daylight illuminant is used. Between 4500K and 5500K a proportional mix of Planckian radiation and the CIE Daylight illuminant is used, according to the following equation:

$$S_{r,M}(\lambda, T_t) = \frac{5500 - T_t}{1000} S_{r,P}(\lambda, T_t) + \left(1 - \frac{5500 - T_t}{1000}\right) S_{r,D}(\lambda, T_t),$$

where $T_t$ is the CCT value, $S_{r,M}(\lambda, T_t)$ is the proportional mix reference illuminant, $S_{r,P}(\lambda, T_t)$ is Planckian radiation, and $S_{r,D}(\lambda, T_t)$ is the CIE Daylight illuminant.

Circadian illuminance (CLA) is a measure of circadian effective light, spectral irradiance distribution of the light incident at the cornea weighted to reflect the spectral sensitivity of the human circadian system as measured by acute melatonin suppression after a one-hour exposure, and CS, which is the effectiveness of the spectrally weighted irradiance at the cornea from threshold (CS=0.1) to saturation (CS=0.7). The values of CLA are scaled such that an incandescent source at 2856K (known as CIE Illuminant A) which produces 1000 lux (visual lux) will produce 1000 units of circadian lux (CLA). CS values are transformed CLA values and correspond to relative melotonian suppression after one hour of light exposure for a 2.3 mm diameter pupil during the mid-point of melotonian production. CS is calculated from $$CS = |0.7\left(1 - \frac{1}{1 + \left(\frac{CLA}{355.7}\right)^{\wedge}1.126}\right).$$

The calculation of CLA is more fully described in Rea et al., "Modelling the spectral sensitivity of the human circadian system," Lighting Research and Technology, 2011; 0: 1-12, and Figueiro et al., "Designing with Circadian Stimulus", October 2016, LD+A Magazine, Illuminating Engineering Society of North America, which are incorporated by reference herein in its entirety for all purposes. Figueiro et al. describe that exposure to a CS of 0.3 or greater at the eye, for at least one hour in the early part of the day, is effective for stimulating the circadian system and is associated with better sleep and improved behavior and mood.

Equivalent Melanopic Lux (EML) provides a measure of photoreceptive input to circadian and neurophysiological light responses in humans, as described in Lucas et al., "Measuring and using light in the melanopsin age." Trends in Neurosciences, January 2014, Vol. 37, No. 1, pages 1-9, which is incorporated by reference herein in its entirety, including all appendices, for all purposes. Melanopic lux is weighted to a photopigment with λmax 480 nm with pre-receptoral filtering based on a 32 year old standard observer, as described more fully in the Appendix A, Supplementary Data to Lucas et al. (2014), User Guide: Irradiance Toolbox (Oxford 18 Oct. 2013), University of Manchester, Lucas Group, which is incorporated by reference herein in its entirety for all purposes. EML values are shown in the tables and Figures herein as the ratio of melanopic lux to luminous flux, with luminous flux considered to be 1000 lumens. It can be desirable for biological effects on users to provide illumination having higher EML in the morning, but lower EML in the late afternoon and evening.

Blue Light Hazard (BLH) provides a measure of potential for a photochemical induced retinal injury that results from radiation exposure. Blue Light Hazard is described in IEC/EN 62471, Photobiological Safety of Lamps and Lamp Systems and Technical Report IEC/TR 62778: Application of IEC 62471 for the assessment of blue light hazard to light sources and luminaires, which are incorporated by reference herein in their entirety for all purposes. A BLH factor can be expressed in (weighted power/lux) in units of $\mu W/cm^2/lux$.

In some aspects the present disclosure relates to lighting devices and methods to provide light having particular vision energy and circadian energy performance. Many figures of merit are known in the art, some of which are described in Ji Hye Oh, Su Ji Yang and Young Rag Do, "Healthy, natural, efficient and tunable lighting: four-package white LEDs for optimizing the circadian effect, color quality and vision performance," Light: Science & Applications (2014) 3: e141-e149, which is incorporated herein in its entirety, including supplementary information, for all purposes. Luminous efficacy of radiation ("LER") can be calculated from the ratio of the luminous flux to the radiant flux (S(λ)), i.e. the spectral power distribution of the light source being evaluated, with the following equation:

$$LER\left(\frac{lm}{W}\right) = 683\left(\frac{lm}{W}\right) \frac{\int V(\lambda) S(\lambda) d\lambda}{\int S(\lambda) d\lambda}.$$

Circadian efficacy of radiation ("CER") can be calculated from the ratio of circadian luminous flux to the radiant flux, with the following equation:

$$CER\left(\frac{blm}{W}\right) = 683\left(\frac{blm}{W}\right) \frac{\int C(\lambda) S(\lambda) d\lambda}{\int S(\lambda) d\lambda}.$$

Circadian action factor ("CAF") can be defined by the ratio of CER to LER, with the following equation:

$$\left(\frac{blm}{lm}\right) = \frac{CER\left(\frac{blm}{W}\right)}{LER\left(\frac{lm}{W}\right)}.$$

The term "blm" refers to biolumens, units for measuring circadian flux, also known as circadian lumens. The term "lm" refers to visual lumens. V(λ) is the photopic spectral luminous efficiency function and C(λ) is the circadian spectral sensitivity function. The calculations herein use the circadian spectral sensitivity function, C(λ), from Gall et al., Proceedings of the CIE Symposium 2004 on Light and Health: Non-Visual Effects, 30 Sep.-2 Oct. 2004; Vienna, Austria 2004. CIE: Wien, 2004, pp 129-132, which is incorporated herein in its entirety for all purposes. By integrating the amount of light (milliwatts) within the circadian spectral sensitivity function and dividing such value by the number of photopic lumens, a relative measure of melatonin suppression effects of a particular light source can be obtained. A scaled relative measure denoted as melatonin suppressing milliwatts per hundred lumens may be obtained by dividing the photopic lumens by 100. The term "melatonin suppressing milliwatts per hundred lumens" consistent with the foregoing calculation method is used throughout this application and the accompanying figures and tables.

The ability of a light source to provide illumination that allows for the clinical observation of cyanosis is based upon the light source's spectral power density in the red portion of the visible spectrum, particularly around 660 nm. The cyanosis observation index ("COI") is defined by AS/NZS 1680.2.5 Interior Lighting Part 2.5: Hospital and Medical Tasks, Standards Australia, 1997 which is incorporated by reference herein in its entirety, including all appendices, for all purposes. COI is applicable for CCTs from about 3300K to about 5500K, and is preferably of a value less than about 3.3. If a light source's output around 660 nm is too low a patient's skin color may appear darker and may be falsely diagnosed as cyanosed. If a light source's output at 660 nm is too high, it may mask any cyanosis, and it may not be diagnosed when it is present. COI is a dimensionless number and is calculated from the spectral power distribution of the light source. The COI value is calculated by calculating the color difference between blood viewed under the test light source and viewed under the reference lamp (a 4000 K Planckian source) for 50% and 100% oxygen saturation and averaging the results. The lower the value of COI, the smaller the shift in color appearance results under illumination by the source under consideration.

The ability of a light source to accurately reproduce color in illuminated objects can be characterized by the Television Lighting Consistency Index ("TLCI-2012" or "TLCI") value Qa, as described fully in EBU Tech 3355, Method for the Assessment of the Colorimetric Properties of Luminaires, European Broadcasting Union ("EBU"), Geneva, Switzerland (2014), and EBU Tech 3355-s1, An Introduction to Spectroradiometry, which are incorporated by reference herein in their entirety, including all appendices, for all purposes. The TLCI compares the test light source to a reference luminaire, which is specified to be one whose chromaticity falls on either the Planckian or Daylight locus and having a color temperature which is that of the CCT of the test light source. If the CCT is less than 3400 K, then a Planckian radiator is assumed. If the CCT is greater than 5000 K, then a Daylight radiator is assumed. If the CCT lies between 3400 K and 5000 K, then a mixed illuminant is assumed, being a linear interpolation between Planckian at 3400 K and Daylight at 5000 K. Therefore, it is necessary to calculate spectral power distributions for both Planckian and Daylight radiators. The mathematics for both operations is known in the art and is described more fully in CIE Technical Report 15:2004, Colorimetry 3$^{rd}$ ed., International Commission on Illumination (2004), which is incorporated herein in its entirety for all purposes.

First Lighting Channels

In some aspects, the present disclosure provides first lighting channels for use in lighting systems. The first lighting channels can have first color points with CCT values between about 4000K and about 6500K. In some implementations, the first color point can have a CCT of about 4000K. In certain implementations, the first color point can have a CCT of about 4000K, about 4100K, about 4200K, about 4300K, about 4400K, about 4500K, about 4600K, about 4700K, about 4800K, about 4900K, about 5000K, about 5100K, about 5200K, about 5300K, about 5400K, about 5500K, about 5600K, about 5700K, about 5800K, about 5900K, about 6000K, about 6100K, about 6200K, about 6300K, about 6400K, or about 6500K.

In some implementations, the first lighting channel can have one or more LEDs having an emission with a first peak wavelength of between about 440 nm and about 510 nm. In certain implementations, the first lighting channel can have one or more LEDs having an emission with a first peak wavelength of about 450 nm.

Figure 7:
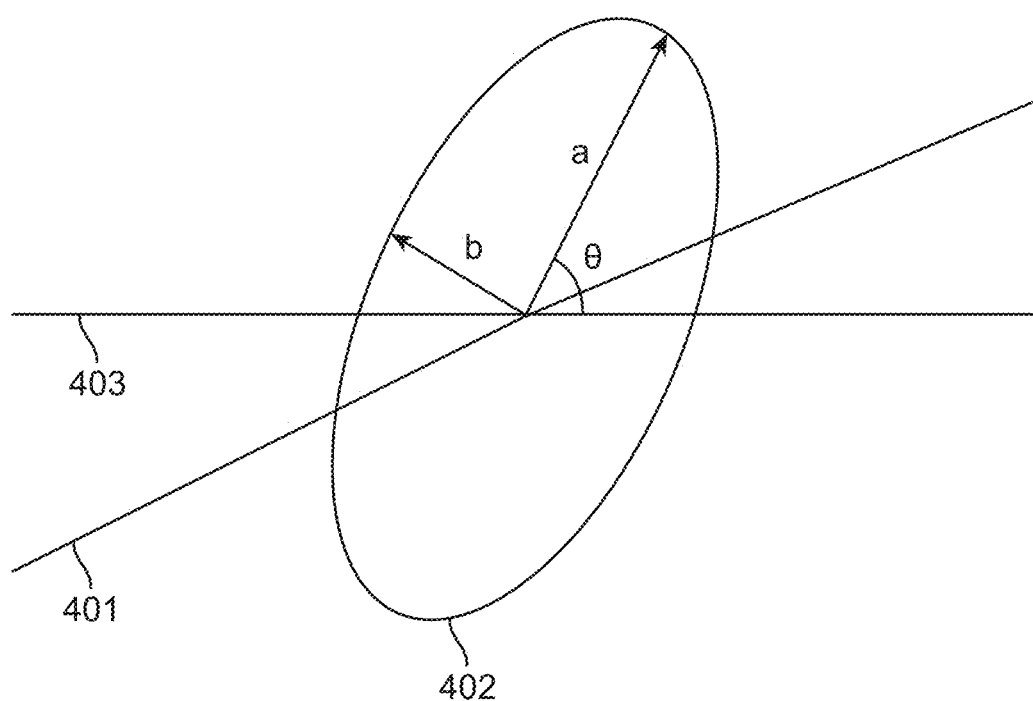
FIG. 7 illustrates some aspects of lighting systems according to the present disclosure, including some suitable color ranges for light generated by components of the devices.

In some implementations, the first lighting channel can have a first color point with a CCT value of about 4000K. The first lighting channel can have a first color point with a color-point range 304A can be defined by a polygonal region on the 1931 CIE Chromaticity Diagram defined by the following ccx, ccy color coordinates: (0.4006, 0.4044), (0.3736, 0.3874), (0.3670, 0.3578), (0.3898, 0.3716), which correlates to an ANSI C78.377-2008 standard 4000K nominal CCT white light with target CCT and tolerance of 3985±275K and target duv and tolerance of 0.001±0.006, as more fully described in American National Standard ANSI C78.377-2008, "Specifications for the Chromaticity of Solid State Lighting Products," National Electrical Manufacturers Association, American National Standard Lighting Group, which is incorporated herein in its entirety for all purposes. In some implementations, suitable color-point ranges for the first color point can be described as MacAdam ellipse color ranges in the 1931 CIE Chromaticity Diagram color space, as illustrated schematically in FIG. 7, which depicts a color-point range 402, the black body locus 401, and a line 403 of constant ccy coordinates on the 1931 CIE Chromaticity Diagram. In FIG. 7, MacAdam ellipse ranges are described with major axis "a", minor axis "b", and ellipse rotation angle θ relative to line 403. In some implementations, the color-point range for the first color point can be range 304B, an embodiment of color range 402, and can be defined as a single 5-step MacAdam ellipse with center point (0.3818, 0.3797) with a major axis "a" of 0.01565, minor axis "b" of 0.00670, with an ellipse rotation angle θ of 52.70°, shown relative to a line 403. In some implementations, the color-point range for the first color point can be range 304C, an embodiment of color range 402, and can be defined as a single 3-step MacAdam ellipse with center point (0.3818, 0.3797) with a major axis "a" of 0.00939, minor axis "b" of 0.00402, with an ellipse rotation angle θ of 53.7°, shown relative to a line 403. In further implementations, the first color point can be within the color-point ranges described in Table 16 for the selected boundary for each nominal CCT value. In other implementations, the color-point range for the first color point can be a region on the 1931 CIE Chromaticity Diagram defined by a polygon connecting the (ccx, ccy) coordinates (0.0.3670, 0.3575), (0.3737, 0.3875), (0.4007, 0.4047), and (0.3898, 0.3720). In yet further implementations, the color-point range for the first color point can be a region on the 1931 CIE Chromaticity Diagram defined by a 4-step MacAdam ellipse centered at 3985K CCT and duv=+0.9845. In other implementations, the color-point range for the first color point can be a region on the 1931 CIE Chromaticity Diagram defined by a polygon connecting the (ccx, ccy) coordinates (0.3703, 0.3590), (0.3851, 0.3679), (0.3942, 0.3972), and (0.3769, 0.3864).

Figure 9:
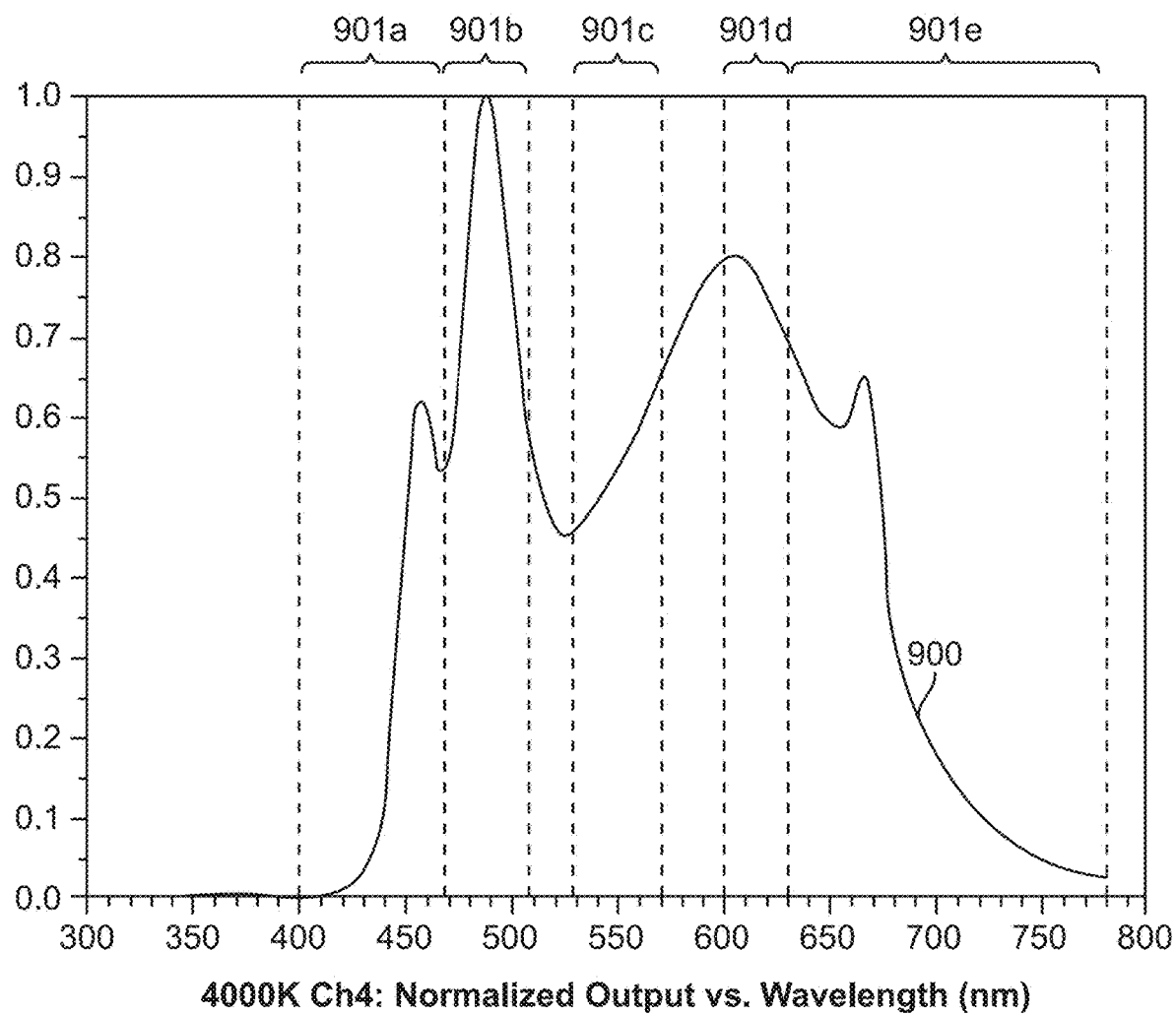
FIG. 9 illustrates some aspects of lighting systems according to the present disclosure, including aspects of spectral power distributions for light generated by components of the devices.
Figure 13:
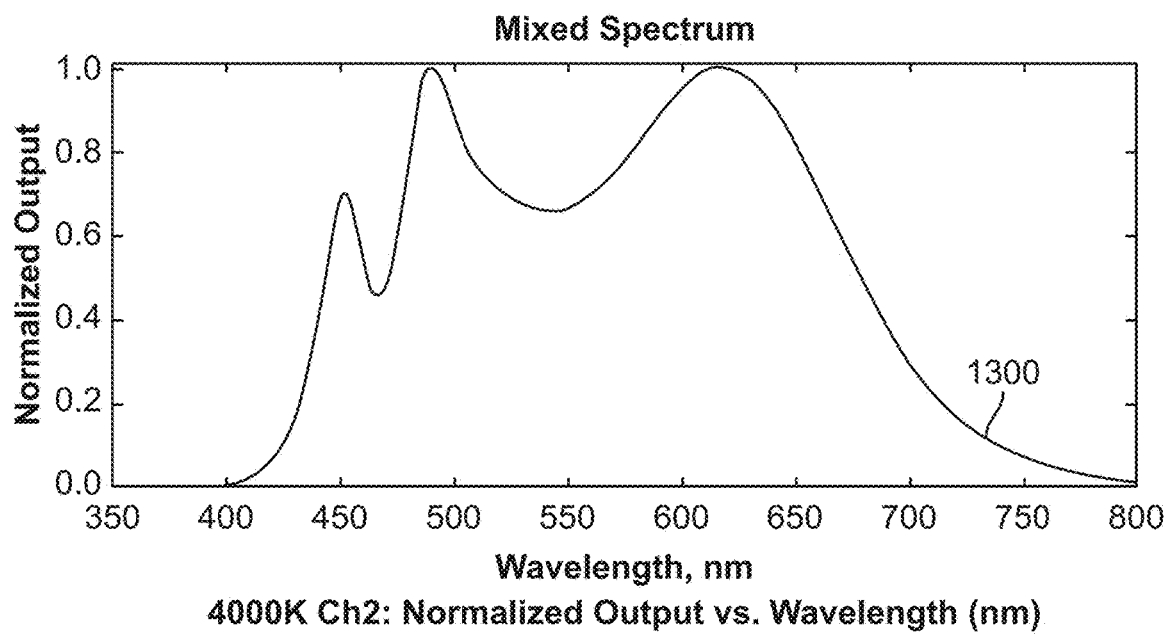
FIG. 13 illustrates some aspects of lighting systems according to the present disclosure, including aspects of spectral power distributions for light generated by components of the devices.
Figure 14:
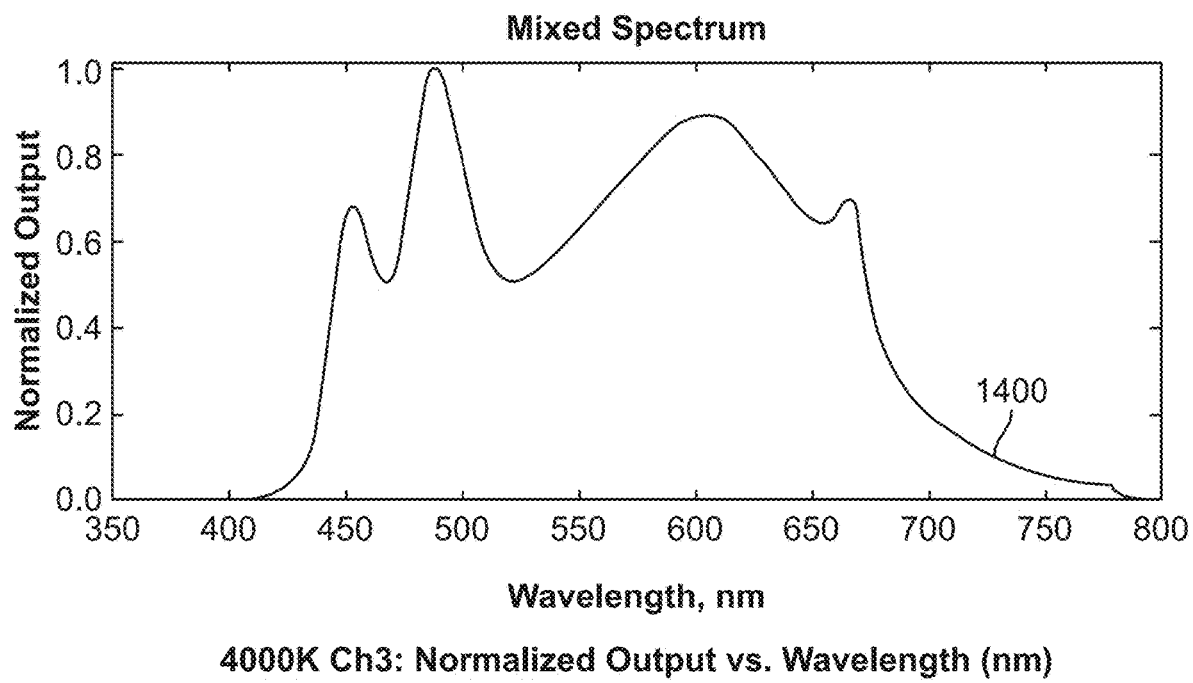
FIG. 14 illustrates some aspects of lighting systems according to the present disclosure, including aspects of spectral power distributions for light generated by components of the devices.
Figure 16:
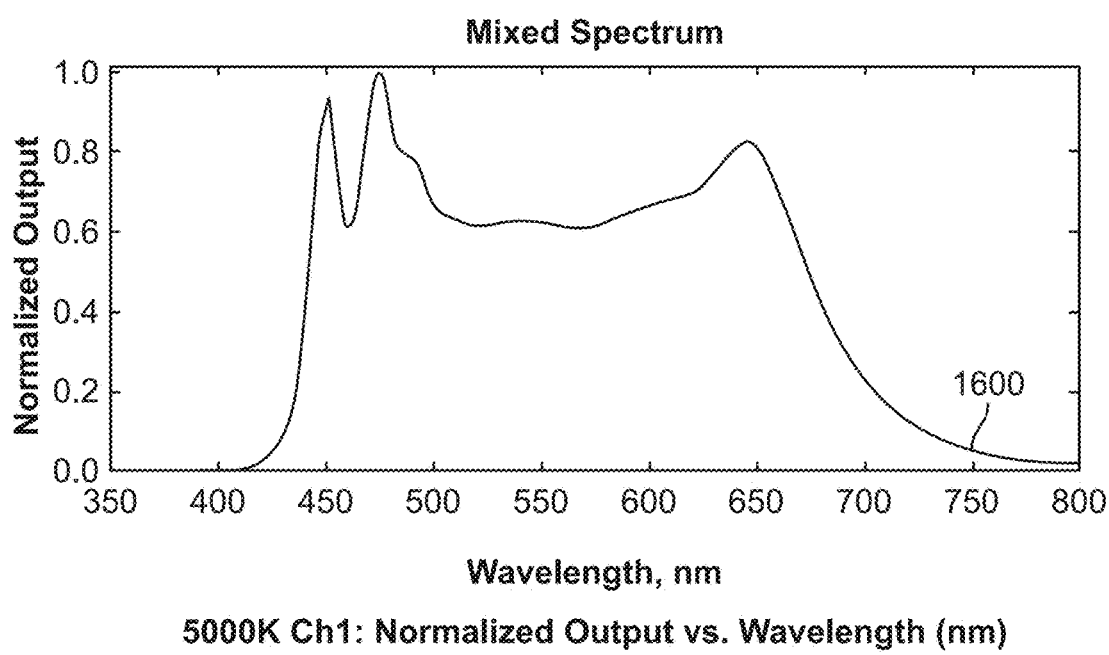
FIG. 16 illustrates some aspects of lighting systems according to the present disclosure, including aspects of spectral power distributions for light generated by components of the devices.

In some implementations, the first lighting channel can have certain spectral power distributions. Some aspects of some exemplary first lighting channels are shown in Table 3. Aspects of the spectral power distributions for the exemplary first lighting channels shown in Table 3 and an average of the exemplary first lighting channels (shown as "Exemplary $1^{st}$ channels avg") are provided in Tables 5, 7, 9, 11, and 12, which show the ratios of spectral power within wavelength ranges, with an arbitrary reference wavelength range selected for each exemplary first lighting channel or average thereof and normalized to a value of 100.0, except for Table 12, in which the values are normalized to a value of 1.000. In certain implementations, the first lighting channel can have a first spectral power distribution with spectral power in one or more of the wavelength ranges other than the reference wavelength range increased or decreased within 30% greater or less, within 20% greater or less, within 10% greater or less, or within 5% greater or less than the values shown in Tables 5, 7, 9, 11, and 12. In some implementations, the first lighting channel can have a spectral power distribution that falls between the minimum (shown as "min") and maximum (shown as "max") values in each of the wavelength ranges as shown in one or more of the Tables 5, 7, 9, 11, and 12. In further implementations, the first lighting channel can have a spectral power distribution that falls between values 5% less, 10% less, 20% less, or 30% less than the minimum (shown as "min") and values 5% more, 10% more, 20% more, or 30% more than the maximum (shown as "max") values in each of the wavelength ranges as shown in one or more of the Tables 5, 7, 9, 11, and 12. FIGS. 9, 13, 14, and 16 depict aspects of first spectral power distributions for the exemplary first lighting channels described herein. FIG. 16 depicts a spectral power distribution 1600 for the exemplary lighting channel "5000K Ch1" listed in Table 3 and further characterized elsewhere herein. FIG. 14 depicts a spectral power distribution 1400 for the exemplary lighting channel "4000K Ch3" listed in Table 3 and further characterized elsewhere herein. FIG. 13 depicts a spectral power distribution 1300 for the exemplary lighting channel "4000K Ch2" listed in Table 3 and further characterized elsewhere herein. FIG. 9 depicts a spectral power distribution 900 for the exemplary lighting channel "4000K Ch4" listed in Table 3 and further characterized elsewhere herein. FIG. 9 further depicts some exemplary wavelength ranges 901A, 901B, 901C, 901D, and 901E, which correspond to the wavelength ranges shown in Table 12. As shown in Table 12, in some implementations, first lighting channels may have particular spectral power values within one or more of wavelength ranges 901A, 901B, 901C, 901D, and 901E, or other wavelength ranges not depicted in FIG. 9 or shown in Table 12 but described elsewhere herein.

Figure 17:
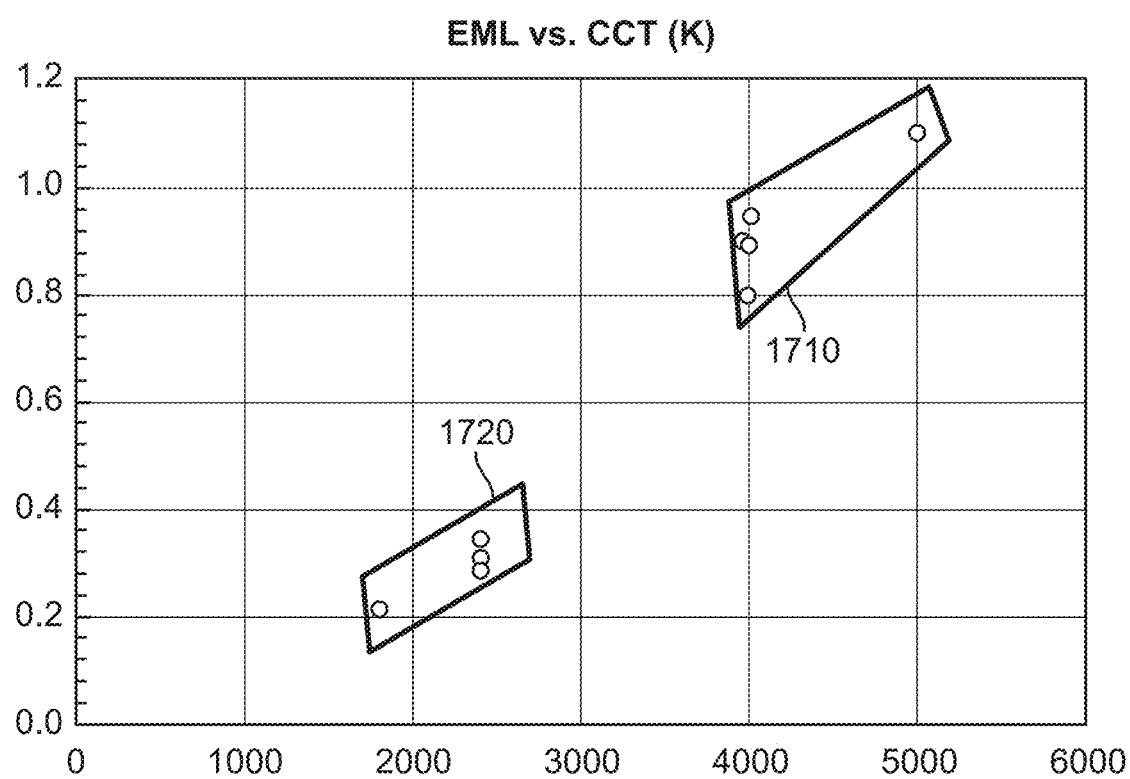
FIG. 17 illustrates some aspects of lighting systems according to the present disclosure, including aspects of spectral power distributions for light generated by components of the devices.

In some aspects, the first lighting channel can have a first white light having a first color point with a CCT and EML value that falls within a range of possible pairings of CCT and EML values, also referred to herein as a CCT-EML range. A suitable CCT-EML range 1710 for first lighting channels of the present disclosure is shown graphically in FIG. 17, which also shows exemplary point pairings of CCT and EML for the exemplary first lighting channels shown in Table 3. Tables 1 and 2 show CCT and EML values for color points generated by some commercially-available fixed-CCT LED-driven white light systems having Ra values of approximately 80.

Second Lighting Channels

In some aspects, the present disclosure provides second lighting channels for use in lighting systems. The second lighting channels can have second color points with CCT values between about 1800K and about 2700K. In some implementations, the first color point can have a CCT of about 2400K. In some implementations, the first color point can have a CCT of about 1800K, about 1900K, about 2000K, about 2100K, about 2200K, about 2300K, about 2400K, about 2500K, about 2600K, or about 2700K.

In some implementations, the second lighting channel can have one or more LEDs having an emission with a second peak wavelength of between about 380 nm and about 420 nm. In certain implementations, the second lighting channel can have one or more LEDs having an emission with a second peak wavelength of about 410 nm. In some aspects, the use of a different peak wavelength for the LEDs in the second lighting channel in comparison to the LEDs in the first lighting channel can contribute to the desired performance of the lighting systems of the disclosure.

In some implementations of the present disclosure, the second lighting channel can produce light having a second color point within a suitable color-point range. In certain implementations, the second color point can be within the color-point ranges described in Table 16 for the selected boundary for each nominal CCT value. In some implementations, the second color point can be within a color-point range defined by a region bounded by a polygon connecting the (ccx, ccy) coordinates on the 1931 CIE Chromaticity Diagram of (0.4593, 0.3944), (0.5046, 0.4007), (0.5262, 0.4381), and (0.4813, 0.4319). In further implementations, the second color point can be within a color-point range defined by a region bounded by a 4-step MacAdam ellipse centered at 2370K CCT value and duv=−0.3. In yet further implementations, the second color point can be within a color-point range defined by a region bounded by a polygon connecting the (ccx, ccy) coordinates on the 1931 CIE Chromaticity Diagram of (0.4745, 0.4025), (0.4880, 0.4035), (0.5036, 0.4254), (0.4880, 0.4244).

Figure 10:
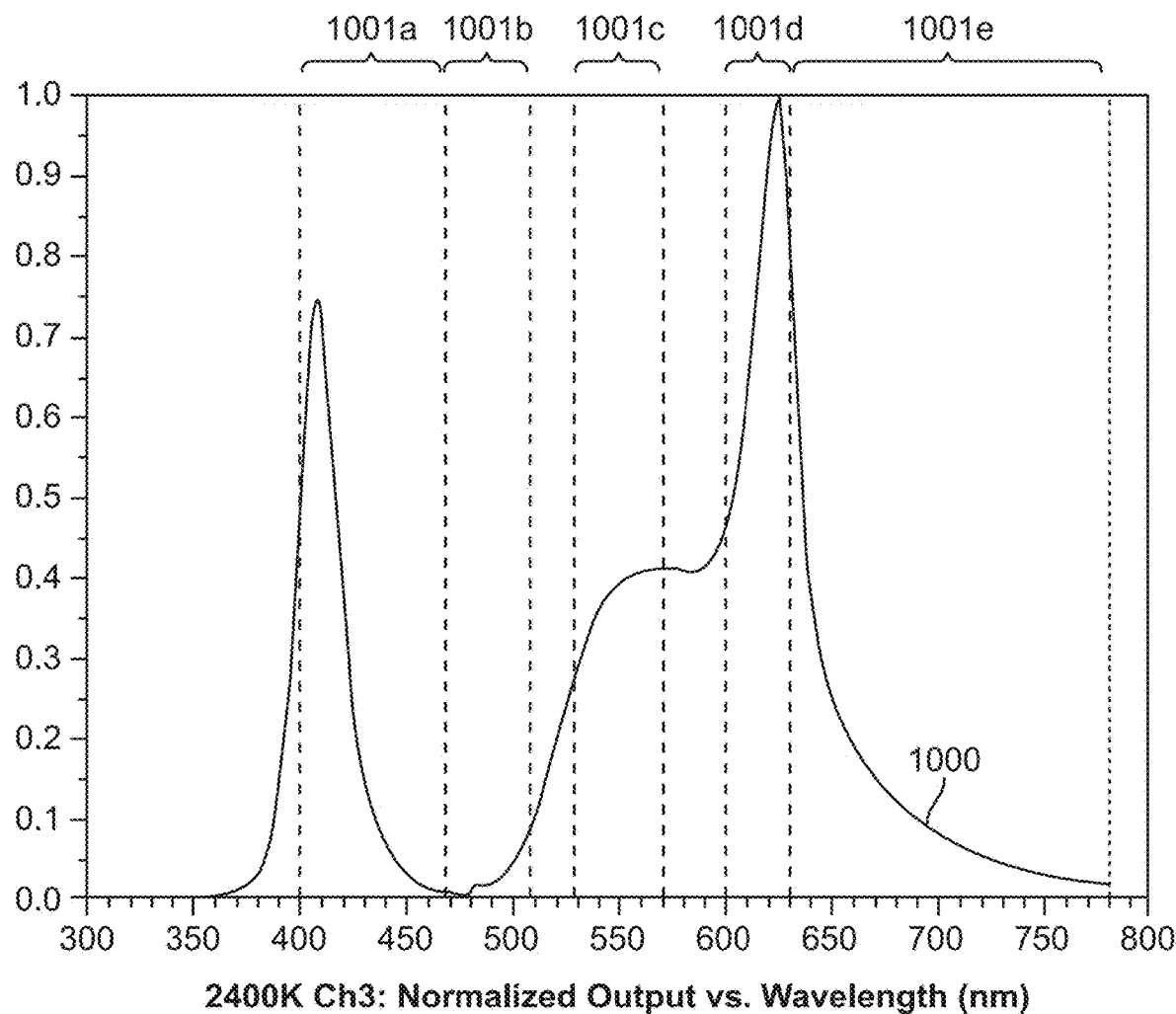
FIG. 10 illustrates some aspects of lighting systems according to the present disclosure, including aspects of spectral power distributions for light generated by components of the devices.
Figure 11:
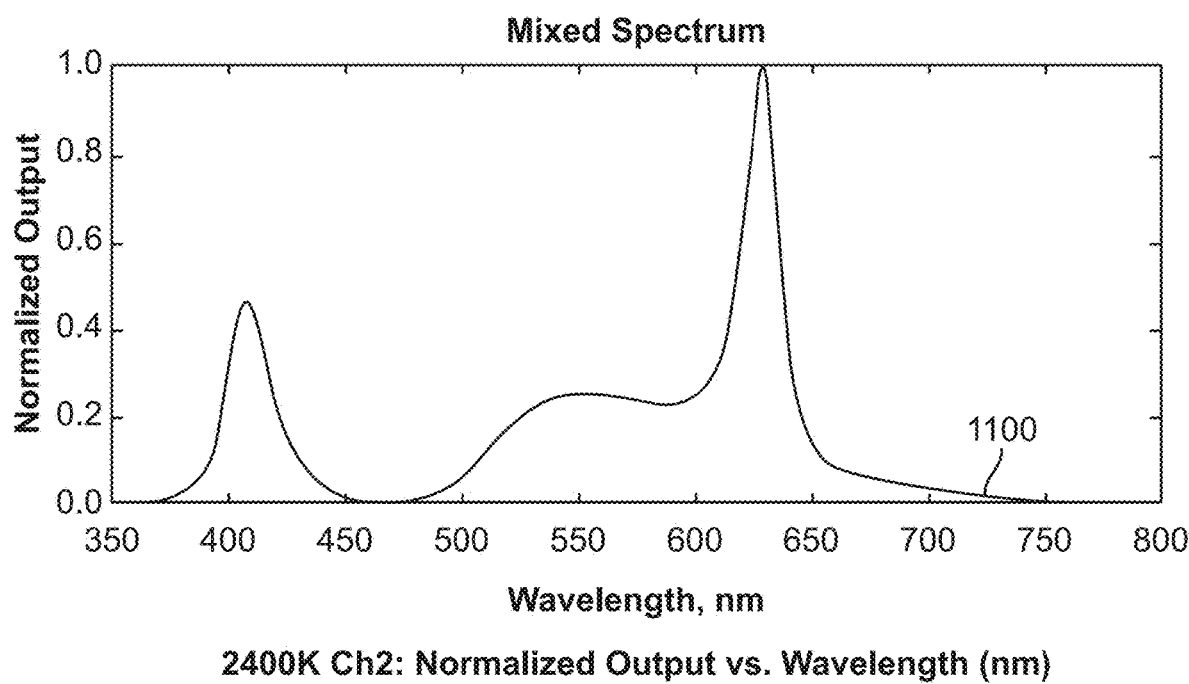
FIG. 11 illustrates some aspects of lighting systems according to the present disclosure, including aspects of spectral power distributions for light generated by components of the devices.
Figure 12:
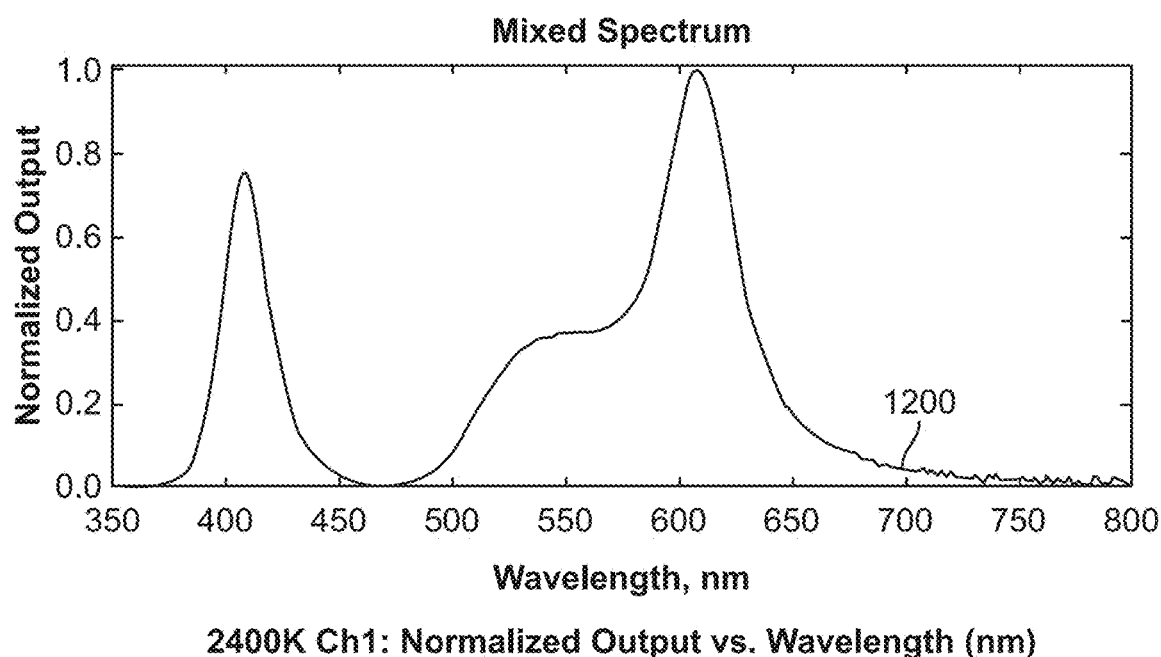
FIG. 12 illustrates some aspects of lighting systems according to the present disclosure, including aspects of spectral power distributions for light generated by components of the devices.
Figure 15:
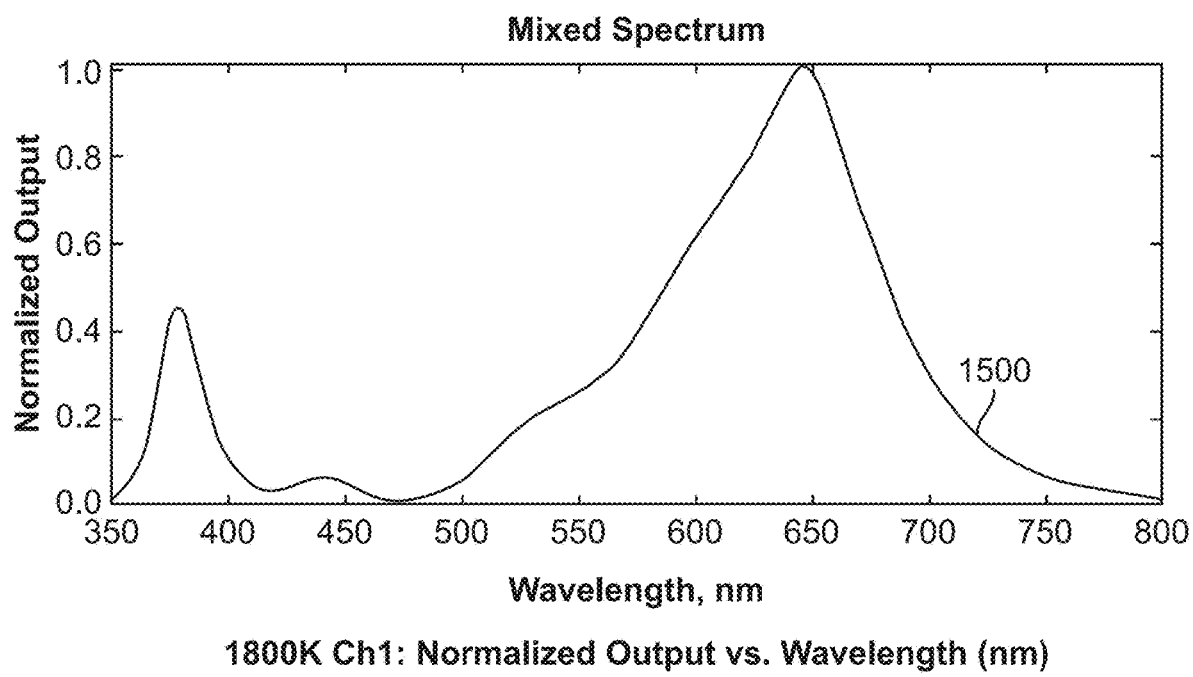
FIG. 15 illustrates some aspects of lighting systems according to the present disclosure, including aspects of spectral power distributions for light generated by components of the devices.

In some implementations, the second lighting channel can have certain spectral power distributions. Some aspects of some exemplary second lighting channels are shown in Table 3. Aspects of the spectral power distributions for the exemplary second lighting channels shown in Table 3 and an average of the exemplary second lighting channels (shown as "Exemplary $2^{nd}$ channels avg") are provided in Tables 4, 6, 8, 10, and 12, which show the ratios of spectral power within wavelength ranges, with an arbitrary reference wavelength range selected for each exemplary second lighting channel or average thereof and normalized to a value of 100.0, except for Table 12, in which the values are normalized to a value of 1.000. In certain implementations, the second lighting channel can have a spectral power distribution with spectral power in one or more of the wavelength ranges other than the reference wavelength range increased or decreased within 30% greater or less, within 20% greater or less, within 10% greater or less, or within 5% greater or less than the values shown in one or more of Tables 4, 6, 8, 10, and 12. In some implementations, the second lighting channel can have a spectral power distribution that falls between the minimum (shown as "min") and maximum (shown as "max") values in each of the wavelength ranges as shown in one or more of the Tables 4, 6, 8, 10, and 12. In further implementations, the second lighting channel can have a spectral power distribution that falls between values 5% less, 10% less, 20% less, or 30% less than the minimum (shown as "min") and values 5% more, 10% more, 20% more, or 30% more than the maximum (shown as "max") values in each of the wavelength ranges as shown in one or more of the Tables 4, 6, 8, 10, and 12. FIG. 11 depicts a spectral power distribution 1100 for the exemplary lighting channel "2400K Ch2" listed in Table 3 and further characterized elsewhere herein. FIG. 12 depicts a spectral power distribution 1200 for the exemplary lighting channel "2400K Ch3" listed in Table 3 and further characterized elsewhere herein. FIG. 15 depicts a spectral power distribution 1500 for the exemplary lighting channel "1800K Ch1" listed in Table 3 and further characterized elsewhere herein. FIG. 10 depicts a spectral power distribution 1000 for the exemplary lighting channel "2400K Ch3" listed in Table 3 and further characterized elsewhere herein. FIG. 10 further depicts some exemplary wavelength ranges 1001A, 1001B, 1001C, 1001D, and 1001E, which correspond to the wavelength ranges shown in Table 12. As shown in Table 12, in some implementations, second lighting channels may have particular spectral power values within one or more of wavelength ranges 1001A, 1001B, 1001C, 1001D, and 1001E, or other wavelength ranges not depicted in FIG. 10 or shown in Table 12 but described elsewhere herein.

In some aspects, the second lighting channel can have a second white light having a second color point with a CCT and EML value that falls within a range of possible pairings of CCT and EML values, also referred to herein as a CCT-EML range. A suitable CCT-EML range 1720 for second lighting channels of the present disclosure is shown graphically in FIG. 17, which also shows exemplary point pairings of CCT and EML for the exemplary second lighting channels shown in Table 3.

Circadian-Stimulating Energy Characteristics

In some aspects of the present disclosure, each of the first, second, and third spectral power distributions can have various circadian-stimulating energy characteristics. By selecting appropriate first and second lighting channels, particular circadian-stimulating effects of the lighting systems can be achieved while also providing excellent color-rendering and other lighting performance.

Figure 4:
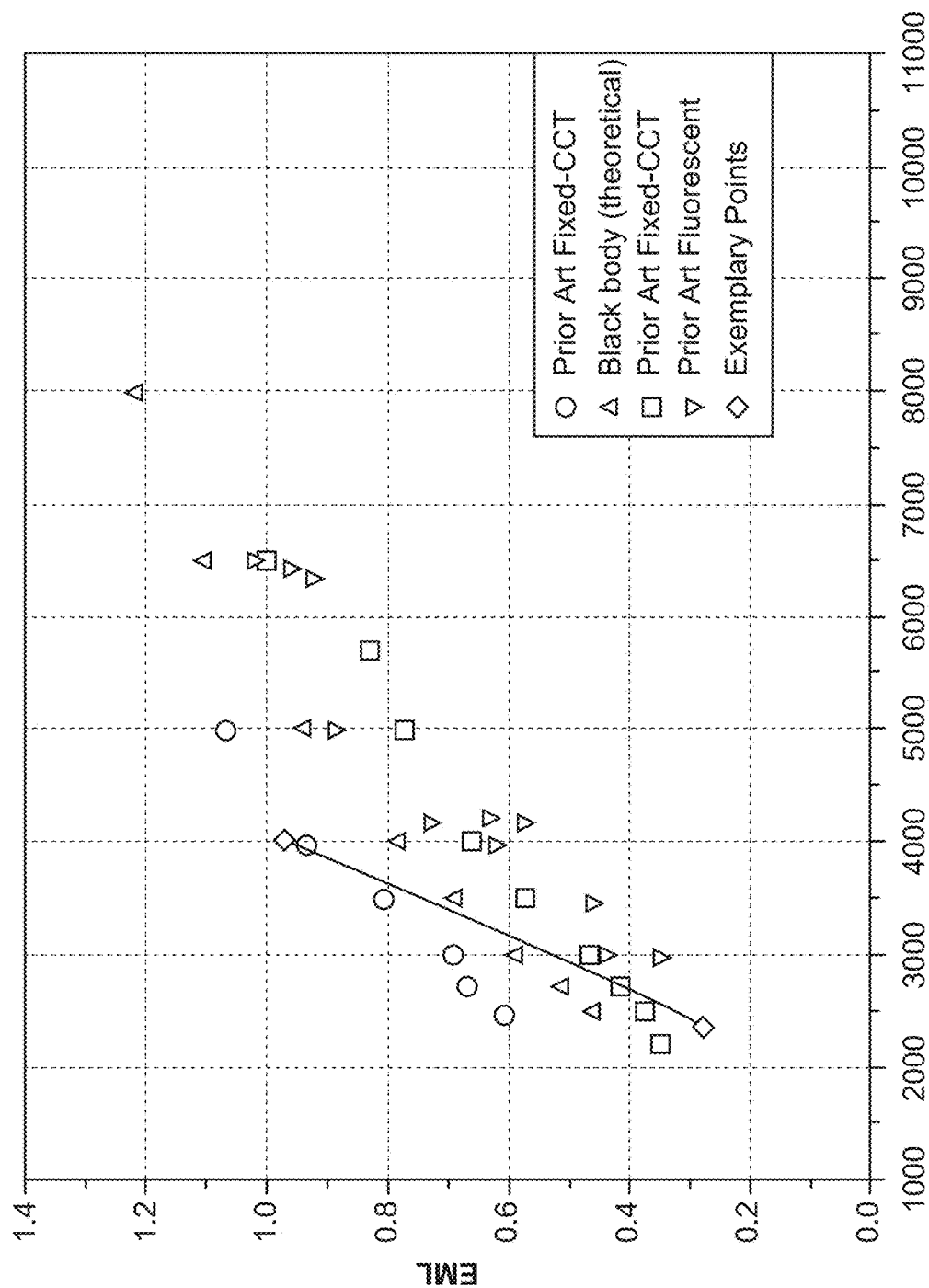
FIG. 4 depicts a graph of aspects of lighting systems of the present disclosure and commercially available lighting systems.

In certain implementations, one or more of the circadian-stimulating energy characteristics of the lighting systems can be EML values of the first, second, and third white light. FIG. 4 graphically shows EML values and CCT values for commercially available LED-based lighting systems having Ra values of approximately 80, fluorescent ("FL") and incandescent lighting systems, and two exemplary color points for implementations of the present disclosure (diamonds connected by solid black line). In some aspects of the present disclosure, the lighting systems can provide a ratio of a first EML value of the first white light to a second EML value of the second white light. In some implementations, the ratio of the first EML value to the second EML value can be between about 2.0 and about 5.5, between about 3.0 and about 5.0, between about 2.8 and about 3.8, between about 2.6 and about 3.3, between about 4.0 and about 5.5, between about 4.5 and about 5.5, between about 5.5 and about 6.5, between about 6.5 and about 7.5, between about 7.5 and about 8.5, between about 8.5 and about 9.5, between about 2.0 and about 10.0, between about 3.0 and about 10.0, between about 4.0 and about 10.0, between about 5.0 and about 10.0, between about 6.0 and about 10.0, between about 7.0 and about 10.0, between about 8.0 and about 10.0, or between about 9.0 and about 10.0. In further implementations, the ratio of the first EML value to the second EML value can be about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, about 9, about 9.1, about 9.2, about 9.3, about 9.4, about 9.5, about 9.6, about 9.7, about 9.8, about 9.9, or about 10.0. Ratios between the exemplary first and second lighting channels shown in Table 3 are shown in Table 14. In certain implementations, the ratio of the first EML value to the second EML value can be greater than about 2.7 with the first lighting channel producing light with a first color point having a CCT of less than or equal to about 5000K. This can be advantageous as it can provide for a desirable change in EML values while avoiding the use of cool white light, which can be undesirable for certain applications and can have higher BLH factors.

Figure 18:
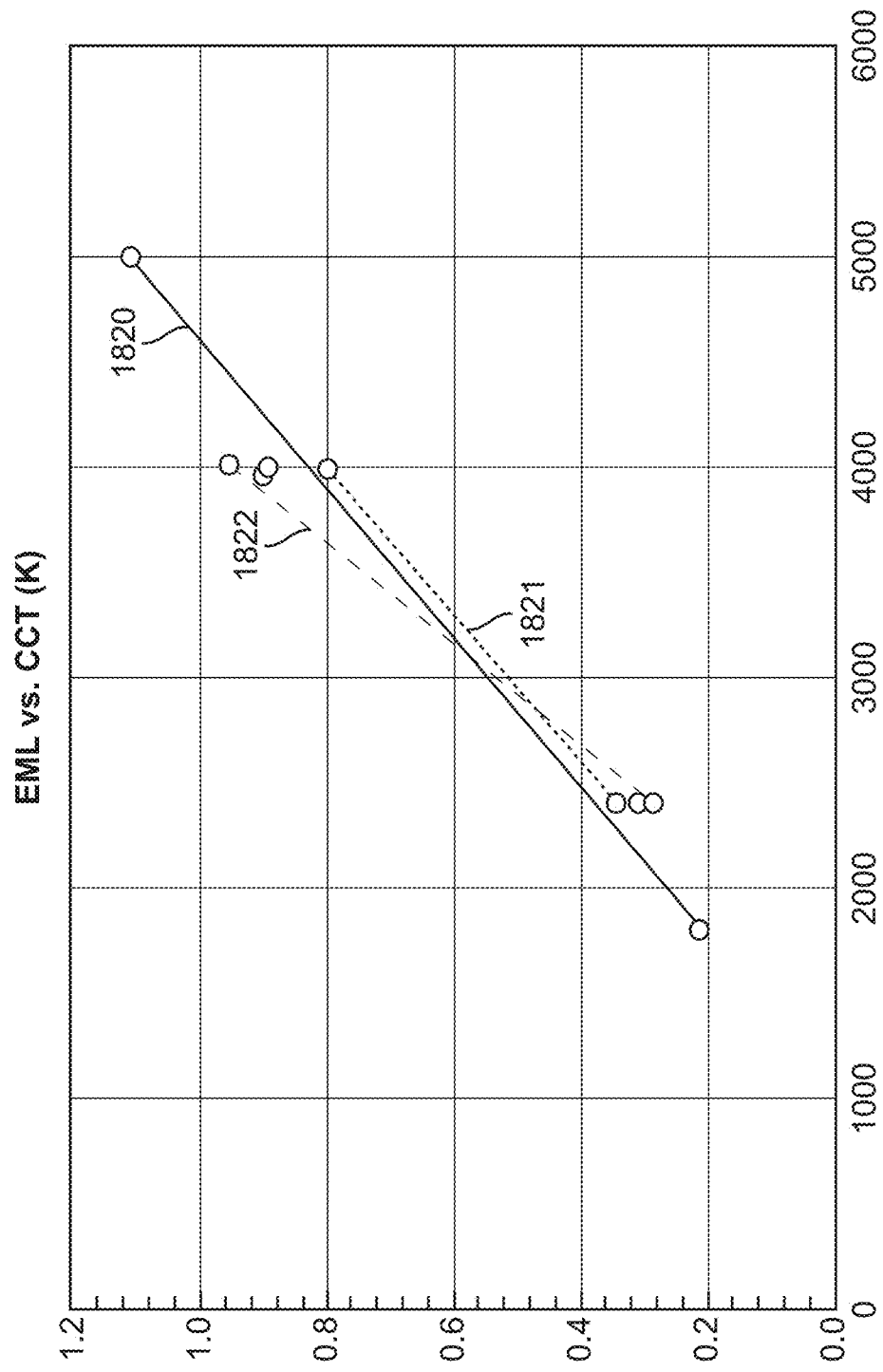
FIG. 18 illustrates aspects of lighting systems according to the present disclosure.

In further aspects of the present disclosure, the lighting systems can provide an EML slope against CCT difference for the first lighting channels and the second lighting channels, also referred to herein as "EML slope." EML slope against CCT difference between pairings of the exemplary first and second lighting channels shown in Table 3 are shown in Table 13, with the slope values shown per 1000K for ease of reading. Some exemplary EML slope lines 1820, 1821, and 1822 are shown graphically in FIG. 18 for pairings for some pairings of the exemplary first lighting channels and second lighting channels listed in Table 3. In some implementations, the EML slope can be between about 0.25 and about 0.45, about 0.30 and about 0.42, about 0.35 and about 0.42, about 0.38 and about 0.42, between about 0.40 and about 0.42, or between about 0.33 and about 0.40. In further implementations, the EML slope can be about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, or about 0.45.

In further aspects of the present disclosure, lighting systems can have first and second lighting channels with first and second circadian-stimulating energy characteristics that relate to spectral energy within particular wavelength ranges. In some implementations, spectral energy concentrations within particular wavelength ranges can lead to biological effects by providing photostimulation to intrinsically photosensitive retinal ganglion cells (ipRGCs), which express melanopsin, a photopigment that can respond to light directly, and can be associated with non-image-forming functions such as circadian photoentrainment and pupil-size control in addition to some image-forming functions. ipRGCs are sensitive to light at wavelengths between about 400 nm and about 600 nm, with a peak sensitivity and response to light with wavelengths around 480 nm to 490 nm. In certain implementations, the first circadian-stimulating energy characteristic and the second circadian-stimulating energy characteristic can be the percentage of the spectral power in the first spectral power distribution and the second spectral power distribution, respectively, between a first wavelength value and a second wavelength value, forming a particular wavelength range therein greater than the first wavelength value and less than or equal to the second wavelength value. In some implementations, the first wavelength value can be about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550, about 560 nm, about 570 nm, about 580 nm, about 590 nm, or about 600 nm. In some implementations, the second wavelength value can be about about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550, about 560 nm, about 570 nm, about 580 nm, about 590 nm, about 600 nm, or about 610 nm. In certain implementations, the first wavelength value can be 440 nm and the second wavelength value can be 490 nm, with the particular wavelength range being $440<\lambda\leq490$ nm, as shown for values for the exemplary first and second lighting channels shown in Table 3, which shows the percent spectral energy in the range $440<\lambda\leq490$ nm in comparison to the total spectral energy in the range $380<\lambda\leq780$ nm. In further implementations, other first and second wavelength values can be selected for the first circadian-stimulating energy characteristic and the second circadian-stimulating energy characteristic of the percentages of the spectral power in the first spectral power distribution and the second spectral power distribution between the first and second wavelength values, including but not limited to wavelength ranges (in nm) from about 400 to about 410, about 410 to about 420, about 420 to about 430, about 430 to about 440, about 440 to about 450, about 450 to about 460, about 460 to about 470, about 470 to about 480, about 480 to about 490, about 490 to about 500, about 500 to about 510, about 510 to about 520, about 520 to about 530, about 530 to about 540, about 540 to about 550, or about 550 to about 560. The percentages of the spectral power in the first spectral power distribution and the second spectral power distribution for a particular wavelength range can be obtained or calculated from the data for the exemplary first and second lighting channels shown in Tables 3-12 and the characteristics of suitable first and second lighting channels as described elsewhere herein. Table 15 shows some values for 10-nm wide wavelength ranges between 400 nm and 520 nm, shown as a percentage of spectral energy in the wavelength range in comparison to the total spectral energy from 320 nm to 800 nm. In some implementations, the first circadian-stimulating energy characteristic can be the percentage of spectral energy in one or more of the wavelength ranges shown in Table 15 for the exemplary first lighting channels of Table 3 or the average thereof ("Exemplary $1^{st}$ channels avg"). In further implementations, the first circadian-stimulating energy characteristic can be between values equal to, 5% less than, 10% less than, 20% less than, or 30% less than the minimum (shown as "Exemplary $1^{st}$ channels min") and values equal to, 5% more than, 10% more than, 20% more than, or 30% more than, the maximum (shown as "Exemplary $1^{st}$ channels max") values in one or more of the wavelength ranges as shown in Table 15. In further implementations, the second circadian-stimulating energy characteristic can be the percentage of the spectral energy in one or more of the wavelength ranges shown in Table 15 for the exemplary second lighting channels of Table 3 or the average thereof ("Exemplary $2^{nd}$ channels avg"). In further implementations, the second circadian-stimulating energy characteristic can be between values equal to, 5% less than, 10% less than, 20% less than, or 30% less than the minimum (shown as "Exemplary $2^{nd}$ channels min") and values equal to, 5% more than, 10% more than, 20% more than, or 30% more than the maximum (shown as "Exemplary $2^{nd}$ channels max") values in one or more of the wavelength ranges as shown in Table 15.

In certain implementations, the first circadian-stimulating energy characteristic and the second circadian-stimulating energy characteristic can be the percentage of the spectral power in the first spectral power distribution and the second spectral power distribution, respectively, between a first wavelength value and a second wavelength value, forming a particular wavelength range therein greater than the first wavelength value and less than or equal to the second wavelength value. In some instances, the first and second circadian-stimulating energy characteristics can be one or more of the percentage of spectral power in the wavelength ranges of 470 nm$<\lambda\leq$480 nm, 480 nm$<\lambda\leq$490 nm, and 490 nm$<\lambda\leq$500 nm in comparison to the total energy from 320 nm$<\lambda\leq$800 nm in the first and second spectral power distributions respectively. In some implementations, for the first lighting channel the percentage of spectral power in the wavelength ranges of 470 nm$<\lambda\leq$480 nm in comparison to the total energy from 320 nm$<\lambda\leq$800 nm can be between about 2.50 and about 6.00, between about 3.00 and about 5.50, between about 3.00 and about 4.00, between about 3.50 and about 4.00, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In certain implementations, for the first lighting channel the percentage of spectral power in the wavelength ranges of 480 nm$<\lambda\leq$490 nm in comparison to the total energy from 320 nm$<\lambda\leq$800 nm can be between about 4.0 and about 6.5, between about 4.5 and about 5.5, between about 4.4 and about 4.6, between about 5.2 and about 5.8, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5. In some implementations, for the first lighting channel the percentage of spectral power in the wavelength ranges of 490 nm$<\lambda\leq$500 nm in comparison to the total energy from 320 nm$<\lambda\leq$800 nm can be between about 3.5 and about 6.0, between about 4.0 and about 5.0, between about 4.5 and about 5.5, between about 4.5 and about 5.0, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In some implementations, for the second lighting channel the percentage of spectral power in the wavelength ranges of 470 nm$<\lambda\leq$480 nm in comparison to the total energy from 320 nm$<\lambda\leq$800 nm can be between about 0.025 and about 0.080, between about 0.030 and about 0.060, between about 0.050 and about 0.070, between about 0.050 and about 0.060, about 0.025, about 0.030, about 0.035, about 0.040, about 0.045, about 0.050, about 0.055, about 0.56, about 0.57, about 0.58, about 0.59, about 0.060, about 0.61, about 0.62, about 0.63, about 0.64, about 0.065, about 0.66, about 0.67, about 0.68, about 0.69, about 0.070, about 0.075, or about 0.080. In certain implementations, for the second lighting channel the percentage of spectral power in the wavelength ranges of 480 nm<λ≤490 nm in comparison to the total energy from 320 nm<λ≤800 nm can be between about 0.10 and about 0.30, between about 0.10 and about 0.15, between about 0.20 and about 0.25, between about 0.13 and about 0.24, about 0.10, about 0.11, about 0.12, about 0.13, about 0.14, about 0.15, about 0.016, about 0.17, about 0.18, about 0.19, about 0.20, about 0.21, about 0.22, about 0.23, about 0.24, about 0.25, about 0.26, about 0.27, about 0.28, about 0.29, or about 0.30. In some implementations, for the second lighting channel the percentage of spectral power in the wavelength ranges of 490 nm<λ≤500 nm in comparison to the total energy from 320 nm<λ≤800 nm can be between about 0.25 and about 0.75, between about 0.25 and about 0.40, between about 0.55 and about 0.70, between about 0.30 and about 0.35, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.67, about 0.68, about 0.69, about 0.70, about 0.71, about 0.72, about 0.73, about 0.74, or about 0.75.

In certain implementations, the first spectral power distribution of the first white light produced by the first lighting channel has a first circadian-stimulating energy characteristic, and the second spectral power distribution of the second white light produced by the second lighting channel has a second circadian-stimulating energy characteristic. In some implementations, the first circadian-stimulating energy characteristic can be a first percentage, the first percentage comprising the percentage of the spectral power between 380 nm and 780 nm in the first spectral power distribution between 440 nm and 490 nm. In certain implementations, the second circadian-stimulating energy characteristic can be a second percentage, the second percentage comprising the percentage of the spectral power between 380 nm and 780 nm in the second spectral power distribution between 440 nm and 490 nm. Table 3 shows some exemplary values for the first and second percentages for exemplary first and second lighting channels. In certain implementations of the lighting systems of the present disclosure, the first percentage can be between about 15% and about 25%, between about 16% and about 22%, about 16%, about 17%, about 18%, about 19%, about 20%, about 21%, about 22%, about 23%, about 24%, or about 25%. In further implementations of the lighting systems of the present disclosure, the second percentage can be between about 0.9% and about 1.05%, between about 0.85% and about 0.95%, between about 0.85% and about 0.90%, between about 0.90% and about 0.95%, about 0.90%, about 0.91%, about 0.92%, about 0.93%, about 0.94%, about 0.95%, about 0.96%, about 0.9'7%, about 0.98%, about 0.99%, about 1.00%, about 1.01%, about 1.02%, about 1.03%, about 1.04%, or about 1.05%. In some implementations, the lighting systems can have a ratio of the first percentage to the second percentage of between about 13 and about 30, between about 15 and about 25, between about 20 and about 25, between about 20 and about 30, between about 18 and about 22, about 13, about 14, about 15, about 16, about 17, about 18, about 19, about 20, about 21, about 22, about 23, about 24, about 25, about 26, about 27, about 28, about 29, or about 30.

In certain aspects, the present disclosure provides lighting systems that can provide the third white light at a plurality of third color points along a predefined path near the black body locus on the 1931 CIE Chromaticity Diagram, with the third color points having particular circadian-stimulating energy characteristics. The third color points can have particular circadian-stimulating energy characteristics at CCT values above or below one or more of a first threshold CCT, a second threshold CCT, or a third threshold CCT or at CCT values between pairs of the first, second, and third threshold CCT values. The second threshold CCT can be about 1800K, about 1900K, about 2000K, about 2100K, about 2200K, about 2300K, about 2400K, about 2500K, about 2600K, about 2700K, about 2800K, about 2900K, about 3000K, about 3100K, or about 3200K. The first threshold CCT can be about 3300K, about 3400K, about 3500K, about 3600K, about 3700K, about 3800K, about 3900K, about 4000K, about 4500K, about 5000K, about 5500K, about 6000K, or about 6500K.

In some implementations, the third color points can have EML values greater than a first EML threshold at CCT values greater than the first threshold CCT and the third color points can have EML values less than a second EML threshold at CCT values less than the second threshold CCT. In certain implementations, the first threshold EML value can be about 0.60 and the first threshold CCT can be about 3300K. In certain implementations, the first threshold EML value can be about 0.60 and the first threshold CCT can be about 3300K. In some implementations, the first threshold EML value can be about 0.75 and the first threshold CCT can be about 3500K. In further implementations, the first threshold EML value can be about 0.85 and the first threshold CCT can be about 3800K. In certain implementations, the second threshold EML value can be about 0.58 and the second threshold CCT can be about 3100K. In certain implementations, the second threshold EML value can be about 0.50 and the second threshold CCT can be about 2900K. In certain implementations, the second threshold EML value can be about 0.43 and the second threshold CCT can be about 2700K. In certain implementations, the second threshold EML value can be about 0.40 and the second threshold CCT can be about 2600K.

Luminescent Materials

Blends of luminescent materials can be used in luminophoric mediums (102A/102B/102A'$_1$/102B'$_1$/102A'$_2$/102B'$_2$/102A'$_3$/102B'$_3$/102A'$_4$/102B'$_4$/102A'$_n$/102B'$_n$) to create luminophoric mediums having the desired saturated color points when excited by their respective LED strings (102A/102B/102A'$_1$/102B'$_1$/102A'$_2$/102B'$_2$/102A'$_3$/102B'$_3$/102A'$_4$/102B'$_4$/102A'$_n$/102B'$_n$) including luminescent materials such as those disclosed in co-pending application PCT/US2016/015318 filed Jan. 28, 2016, entitled "Compositions for LED Light Conversions", the entirety of which is hereby incorporated by this reference as if fully set forth herein. Traditionally, a desired combined output light can be generated along a tie line between the LED string output light color point and the saturated color point of the associated recipient luminophoric medium by utilizing different ratios of total luminescent material to the encapsulant material in which it is incorporated. Increasing the amount of luminescent material in the optical path will shift the output light color point towards the saturated color point of the luminophoric medium. In some instances, the desired saturated color point of a recipient luminophoric medium can be achieved by blending two or more luminescent materials in a ratio. The appropriate ratio to achieve the desired saturated color point can be determined via methods known in the art. Generally speaking, any blend of luminescent materials can be treated as if it were a single luminescent material, thus the ratio of luminescent materials in the blend can be adjusted to continue to meet a target CIE value for LED strings having different peak emission wavelengths. Luminescent materials can be tuned for the desired excitation in response to the selected LEDs used in the LED strings (101A/101B/ 101A'$_1$/101B'$_1$/101A'$_2$/101B'$_2$/101A'$_3$/101B'$_3$/101A'$_4$/ 101B'$_4$/101A'$_n$/101B'$_n$), which may have different peak emission wavelengths within the range of from about 360 nm to about 535 nm. Suitable methods for tuning the response of luminescent materials are known in the art and may include altering the concentrations of dopants within a phosphor, for example. In some implementations of the present disclosure, luminophoric mediums can be provided with combinations of two types of luminescent materials. The first type of luminescent material emits light at a peak emission between about 515 nm and about 590 nm in response to the associated LED string emission. The second type of luminescent material emits at a peak emission between about 590 nm and about 700 nm in response to the associated LED string emission. In some instances, the luminophoric mediums disclosed herein can be formed from a combination of at least one luminescent material of the first and second types described in this paragraph. In implementations, the luminescent materials of the first type can emit light at a peak emission at about 515 nm, 525 nm, 530 nm, 535 nm, 540 nm, 545 nm, 550 nm, 555 nm, 560 nm, 565 nm, 570 nm, 575 nm, 580 nm, 585 nm, or 590 nm in response to the associated LED string emission. In preferred implementations, the luminescent materials of the first type can emit light at a peak emission between about 520 nm to about 555 nm. In implementations, the luminescent materials of the second type can emit light at a peak emission at about 590 nm, about 595 nm, 600 nm, 605 nm, 610 nm, 615 nm, 620 nm, 625 nm, 630 nm, 635 nm, 640 nm, 645 nm, 650 nm, 655 nm, 670 nm, 675 nm, 680 nm, 685 nm, 690 nm, 695 nm, or 700 nm in response to the associated LED string emission. In preferred implementations, the luminescent materials of the first type can emit light at a peak emission between about 600 nm to about 670 nm. Some exemplary luminescent materials of the first and second type are disclosed elsewhere herein and referred to as Compositions A-F. Table 17 shows aspects of some exemplar luminescent materials and properties.

Blends of Compositions A-F can be used in luminophoric mediums (101A/101B/101A'$_1$/101B'$_1$/101A'$_2$/101B'$_2$/ 101A'$_3$/101B'$_3$/101A'$_4$/101B'$_4$/101A'$_n$/101B'$_n$) to create luminophoric mediums having the desired saturated color points when excited by their respective LED strings (101A/ 101B/101C/101D). In some implementations, one or more blends of one or more of Compositions A-F can be used to produce luminophoric mediums (102A/102B/102C/102D). In some preferred implementations, one or more of Compositions A, B, and D and one or more of Compositions C, E, and F can be combined to produce luminophoric mediums (101A/101B/101A'$_1$/101B'$_1$/101A'$_2$/101B'$_2$/101A'$_3$/101B'$_3$/ 101A'$_4$/101B'$_4$/101A'$_n$/101B'$_n$). In some preferred implementations, the encapsulant for luminophoric mediums (101A/101B/101A'$_1$/101B'$_1$/101A'$_2$/101B'$_2$/101A'$_3$/101B'$_3$/ 101A'$_4$/101B'$_4$/101A'$_n$/101B'$_n$) comprises a matrix material having density of about 1.1 mg/mm$^3$ and refractive index of about 1.545 or from about 1.4 to about 1.6. In some implementations, Composition A can have a refractive index of about 1.82 and a particle size from about 18 micrometers to about 40 micrometers. In some implementations, Composition B can have a refractive index of about 1.84 and a particle size from about 13 micrometers to about 30 micrometers. In some implementations, Composition C can have a refractive index of about 1.8 and a particle size from about 10 micrometers to about 15 micrometers. In some implementations, Composition D can have a refractive index of about 1.8 and a particle size from about 10 micrometers to about 15 micrometers. Suitable phosphor materials for Compositions A, B, C, and D are commercially available from phosphor manufacturers such as Mitsubishi Chemical Holdings Corporation (Tokyo, Japan), Intematix Corporation (Fremont, Calif.), EMD Performance Materials of Merck KGaA (Darmstadt, Germany), and PhosphorTech Corporation (Kennesaw, Ga.).

In certain implementations, the luminophoric mediums can include luminescent materials that comprise one or more quantum materials. Throughout this specification, the term "quantum material" means any luminescent material that includes: a quantum dot; a quantum wire; or a quantum well. Some quantum materials may absorb and emit light at spectral power distributions having narrow wavelength ranges, for example, wavelength ranges having spectral widths being within ranges of between about 25 nanometers and about 50 nanometers. In examples, two or more different quantum materials may be included in a lumiphor, such that each of the quantum materials may have a spectral power distribution for light emissions that may not overlap with a spectral power distribution for light absorption of any of the one or more other quantum materials. In these examples, cross-absorption of light emissions among the quantum materials of the lumiphor may be minimized. Throughout this specification, the term "quantum dot" means: a nanocrystal made of semiconductor materials that are small enough to exhibit quantum mechanical properties, such that its excitons are confined in all three spatial dimensions. Throughout this specification, the term "quantum wire" means: an electrically conducting wire in which quantum effects influence the transport properties. Throughout this specification, the term "quantum well" means: a thin layer that can confine (quasi-)particles (typically electrons or holes) in the dimension perpendicular to the layer surface, whereas the movement in the other dimensions is not restricted.

EXAMPLES

General Simulation Method.

Exemplary first and second lighting channels, and lighting systems having pairs of first and second lighting channels, were simulated. For each lighting channel, LED strings and recipient luminophoric mediums with particular emissions were selected, and then spectral power distributions and various light rendering characteristics and circadian-stimulating energy characteristics were calculated. Ra, R9, R13, R15, LER, Rf, Rg, CLA, CS, EML, BLH factor, CAF, CER, COI, GAI, GAI15, GAIBB, and circadian-stimulating energy characteristics were calculated at each representative point. Characteristics and aspects of the spectral power distributions are shown in Tables 3-12 and FIGS. 9-16.

The calculations were performed with Scilab (Scilab Enterprises, Versailles, France), LightTools (Synopsis, Inc., Mountain View, Calif.), and custom software created using Python (Python Software Foundation, Beaverton, Oreg.). Each lighting channel was simulated with an LED emission spectrum and excitation and emission spectra of luminophoric medium(s). The luminophoric mediums can comprise luminescent compositions of phosphors, quantum dots, or combinations thereof, with simulations performed based on absorption/emission spectrums and particle sizes. The exemplary first lighting channels were simulated using spectra of LEDs having peak wavelengths of between about 440 nm and about 510 nm, such as a 450 nm peak wavelength blue LED, one or more LUXEON Z Color Line royal blue LEDs (product code LXZ1-PR01) of color bin codes 3, 4, 5, or 6 (Lumileds Holding B.V., Amsterdam, Netherlands), one or more LUXEON Z Color Line blue LEDs (LXZ1-PB01) of color bin code 1 or 2 (Lumileds Holding B.V., Amsterdam, Netherlands), one or more LUXEON royal blue LEDs (product code LXML-PR01 and LXML-PR02) of color bins 3, 4, 5, or 6 (Lumileds Holding B.V., Amsterdam, Netherlands), one or more LUXEON Rebel Blue LEDs (LXML-PB01, LXML-PB02) of color bins 1, 2, 3, 4, or 5 (Lumileds Holding B.V., Amsterdam, Netherlands), or one or more LUXEON Rebel Cyan LEDs (LXML-PE01) of color bins 1, 2, 3, 4, or 5 (Lumileds Holding B.V., Amsterdam, Netherlands), for example. The exemplary second lighting channels were simulated using spectra of LEDs having peak wavelengths of between about 380 nm and about 420 nm, such as one or more 410 nm peak wavelength violet LEDs, one or more LUXEON Z UV LEDs (product codes LHUV-0380-, LHUV-0385-, LHUV-0390-, LHUV-0395-, LHUV-0400-, LHUV-0405-, LHUV-0410-, LHUV-0415-, LHUV-0420-,) (Lumileds Holding B.V., Amsterdam, Netherlands), one or more LUXEON UV FC LEDs (product codes LxF3-U410) (Lumileds Holding B.V., Amsterdam, Netherlands), one or more LUXEON UV U LEDs (product code LHUV-0415-) (Lumileds Holding B.V., Amsterdam, Netherlands), for example. Similar LEDs from other manufacturers such as OSRAM GmbH and Cree, Inc. that provide a saturated output at the desired peak wavelengths could also be used.

The emission, excitation and absorption curves for phosphors and quantum dots are available from commercial manufacturers such as Mitsubishi Chemical Holdings Corporation (Tokyo, Japan), Intematix Corporation (Fremont, Calif.), EMD Performance Materials of Merck KGaA (Darmstadt, Germany), and PhosphorTech Corporation (Kennesaw, Ga.). The luminophoric mediums used in the first and second lighting channels were simulated as combinations of one or more of luminescent compositions as described more fully elsewhere herein. Those of skill in the art appreciate that various combinations of LEDs and luminescent blends can be combined to generate combined emissions with desired color points on the 1931 CIE chromaticity diagram and the desired spectral power distributions.

Example 1

A lighting system was simulated having a first lighting channel having the characteristics shown as "4000K Ch1" in Tables 3, 5, 7, 9, 11, 12, and 15 and a second lighting channel having the characteristics shown as "2400K Ch1" in Tables 3, 4, 6, 8, 10, 12, and 15 and in FIG. 12. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 2

A lighting system was simulated having a first lighting channel having the characteristics shown as "4000K Ch2" in Tables 3, 5, 7, 9, 11, 12, and 15 and in FIG. 13, and a second lighting channel having the characteristics shown as "2400K Ch1" in Tables 3, 4, 6, 8, 10, 12, and 15 and in FIG. 12. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 3

A lighting system was simulated having a first lighting channel having the characteristics shown as "4000K Ch3" in Tables 3, 5, 7, 9, 11, 12, and 15 and in FIG. 14, and a second lighting channel having the characteristics shown as "2400K Ch1" in Tables 3, 4, 6, 8, 10, 12, and 15 and in FIG. 12. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 4

A lighting system was simulated having a first lighting channel having the characteristics shown as "4000K Ch4" in Tables 3, 5, 7, 9, 11, 12, and 15 and in FIG. 9, and a second lighting channel having the characteristics shown as "2400K Ch1" in Tables 3, 4, 6, 8, 10, 12, and 15 and in FIG. 12. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 5

A lighting system was simulated having a first lighting channel having the characteristics shown as "5000K Ch1" in Tables 3, 5, 7, 9, 11, 12, and 15 and in FIG. 16, and a second lighting channel having the characteristics shown as "2400K Ch1" in Tables 3, 4, 6, 8, 10, 12, and 15 and in FIG. 12. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 6

A lighting system was simulated having a first lighting channel having the characteristics shown as "4000K Ch1" in Tables 3, 5, 7, 9, 11, 12, and 15 and a second lighting channel having the characteristics shown as "2400K Ch2" in Tables 3, 4, 6, 8, 10, 12, and 15 and in FIG. 11. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 7

A lighting system was simulated having a first lighting channel having the characteristics shown as "4000K Ch2" in Tables 3, 5, 7, 9, 11, 12, and 15 and in FIG. 13, and a second lighting channel having the characteristics shown as "2400K Ch2" in Tables 3, 4, 6, 8, 10, 12, and 15 and in FIG. 11. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 8

A lighting system was simulated having a first lighting channel having the characteristics shown as "4000K Ch3" in Tables 3, 5, 7, 9, 11, 12, and 15 and in FIG. 14, and a second lighting channel having the characteristics shown as "2400K Ch2" in Tables 3, 4, 6, 8, 10, 12, and 15 and in FIG. 11. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 9

A lighting system was simulated having a first lighting channel having the characteristics shown as "4000K Ch4" in Tables 3, 5, 7, 9, 11, 12, and 15 and in FIG. 9, and a second lighting channel having the characteristics shown as "2400K Ch2" in Tables 3, 4, 6, 8, 10, 12, and 15 and in FIG. 11. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 10

A lighting system was simulated having a first lighting channel having the characteristics shown as "5000K Ch1" in Tables 3, 5, 7, 9, 11, 12, and 15 and in FIG. 16, and a second lighting channel having the characteristics shown as "2400K Ch2" in Tables 3, 4, 6, 8, 10, 12, and 15 and in FIG. 11. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 11

A lighting system was simulated having a first lighting channel having the characteristics shown as "4000K Ch1" in Tables 3, 5, 7, 9, 11, 12, and 15 and a second lighting channel having the characteristics shown as "2400K Ch3" in Tables 3, 4, 6, 8, 10, 12, and 15 and in FIG. 10. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 12

A lighting system was simulated having a first lighting channel having the characteristics shown as "4000K Ch2" in Tables 3, 5, 7, 9, 11, 12, and 15 and in FIG. 13, and a second lighting channel having the characteristics shown as "2400K Ch3" in Tables 3, 4, 6, 8, 10, 12, and 15 and in FIG. 10. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 13

A lighting system was simulated having a first lighting channel having the characteristics shown as "4000K Ch3" in Tables 3, 5, 7, 9, 11, 12, and 15 and in FIG. 14, and a second lighting channel having the characteristics shown as "2400K Ch3" in Tables 3, 4, 6, 8, 10, 12, and 15 and in FIG. 10. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 14

A lighting system was simulated having a first lighting channel having the characteristics shown as "4000K Ch4" in Tables 3, 5, 7, 9, 11, 12, and 15 and in FIG. 9, and a second lighting channel having the characteristics shown as "2400K Ch3" in Tables 3, 4, 6, 8, 10, 12, and 15 and in FIG. 10. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 15

A lighting system was simulated having a first lighting channel having the characteristics shown as "5000K Ch1" in Tables 3, 5, 7, 9, 11, 12, and 15 and in FIG. 16, and a second lighting channel having the characteristics shown as "2400K Ch3" in Tables 3, 4, 6, 8, 10, 12, and 15 and in FIG. 10. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 16

A lighting system was simulated having a first lighting channel having the characteristics shown as "4000K Ch1" in Tables 3, 5, 7, 9, 11, 12, and 15 and a second lighting channel having the characteristics shown as "1800K Ch1" in Tables 3, 4, 6, 8, 10, 12, and 15 and in FIG. 15. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 17

A lighting system was simulated having a first lighting channel having the characteristics shown as "4000K Ch2" in Tables 3, 5, 7, 9, 11, 12, and 15 and in FIG. 13, and a second lighting channel having the characteristics shown as "1800K Ch1" in Tables 3, 4, 6, 8, 10, 12, and 15 and in FIG. 15. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 18

A lighting system was simulated having a first lighting channel having the characteristics shown as "4000K Ch3" in Tables 3, 5, 7, 9, 11, 12, and 15 and in FIG. 14, and a second lighting channel having the characteristics shown as "1800K Ch1" in Tables 3, 4, 6, 8, 10, 12, and 15 and in FIG. 15. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 19

A lighting system was simulated having a first lighting channel having the characteristics shown as "4000K Ch4" in Tables 3, 5, 7, 9, 11, 12, and 15 and in FIG. 9, and a second lighting channel having the characteristics shown as "1800K Ch1" in Tables 3, 4, 6, 8, 10, 12, and 15 and in FIG. 15. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 20

A lighting system was simulated having a first lighting channel having the characteristics shown as "5000K Ch1" in Tables 3, 5, 7, 9, 11, 12, and 15 and in FIG. 16, and a second lighting channel having the characteristics shown as "1800K Ch1" in Tables 3, 4, 6, 8, 10, 12, and 15 and in FIG. 15. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 21

A lighting system was simulated having a first lighting channel having the characteristics shown as "5000K Ch1" in Tables 3, 5, 7, 9, 11, 12, and 15 and in FIG. 16, and a second lighting channel having the characteristics shown as "1800K Ch1" in Tables 3, 4, 6, 8, 10, 12, and 15 and in FIG. 15. The values for EML slope and EML ratio for this pair of first and second lighting channels are shown in Tables 13 and 14. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 22

A lighting system was simulated having a first lighting channel having the characteristics shown as "Exemplary 1st channels avg" in Tables 3, 5, 7, 9, 11, 12, and 15, and a second lighting channel having the characteristics shown as "Exemplary 2nd channels avg" in Tables 3, 4, 6, 8, 10, 12, and 15. The first lighting channel has a first color point at (0.3735, 0.3719) ccx, ccy coordinates. The second lighting channel has a second color point at (0.5021, 0.4137) ccx, ccy coordinates. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

TABLE 1

EML performance for commercially-available fixed-CCT LED lighting systems

| CCT | EML |
|---|---|
| 6500K | 1.350 |

TABLE 1-continued

EML performance for commercially-available fixed-CCT LED lighting systems

| CCT | EML |
|---|---|
| 5000K | 1.066 |
| 4000K | 0.935 |
| 3500K | 0.807 |
| 3000K | 0.690 |
| 2700K | 0.665 |
| 2500K | 0.603 |
| 2400K | 0.572 |

TABLE 2

EML performance for commercially-available fixed-CCT LED lighting systems

| CCT | EML |
|---|---|
| 2200K | 0.347999 |
| 2400K | 0.3654583 |
| 2500K | 0.37418788 |
| 2700K | 0.4134712 |
| 3000K | 0.4675737 |
| 3500K | 0.5702719 |
| 4000K | 0.6567719 |
| 5000K | 0.7748765 |
| 5700K | 0.8203205 |
| 6500K | 0.9977367 |

TABLE 3

| | x | y | CCT | duv | Ra | R9 | R13 | R15 | LER | COI | GAI | GAI 15 | GAI_BB |
|---|---|---|---|---|---|---|---|---|---|---|---|---|---|
| 2400K Ch1 | 0.4872 | 0.4166 | 2401.7 | 0.62 | 76.39 | 50.16 | 81.3 | 61.64 | 312.32 | 10.53 | 36.61 | 89.03 | 83.17 |
| 2400K Ch2 | 0.4858 | 0.4148 | 2404.69 | 0.07 | 86.38 | 92.09 | 95.28 | 89.70 | 282.76 | 9.68 | 44.51 | 102.45 | 95.46 |
| 2400K Ch3 | 0.4852 | 0.4137 | 2403.72 | −0.29 | 80.60 | 35.83 | 84.04 | 81.58 | 282.07 | 7.79 | 41.87 | 100.73 | 93.95 |
| 1800K Ch1 | 0.5503 | 0.4097 | 1801 | 0.49 | 90.94 | 62.65 | 92.01 | 87.32 | 210.12 | 16.00 | 17.37 | 47.81 | 94.05 |
| 4000K Ch1 | 0.3807 | 0.3772 | 3995.74 | 0.16 | 91.18 | 58.05 | 90.71 | 86.30 | 292.50 | | 82.78 | 219.40 | 105.73 |
| 4000K Ch2 | 0.3803 | 0.3766 | 4003.12 | −0.02 | 88.67 | 96.86 | 89.72 | 94.57 | 274.59 | 1.2 | 76.69 | 200.10 | 96.28 |
| 4000K Ch3 | 0.3814 | 0.3758 | 3967.48 | −0.7 | 86.26 | 70.93 | 95.39 | 93.30 | 283.64 | 3.07 | 71.86 | 189.40 | 91.81 |
| 4000K Ch4 | 0.3804 | 0.3782 | 4012.69 | 0.72 | 82.45 | 79.82 | 91.17 | 92.69 | 280.02 | 2.4 | 69.51 | 182.68 | 87.72 |
| 5000K Ch1 | 0.3449 | 0.3516 | 5007 | 0.08 | 83.73 | 56.73 | 82.41 | 82.71 | 257.55 | 0.81 | 90.61 | 234.15 | 96.76 |

| | Circadian power [mW] | Circadian flux | CER (Circadian power per flux) [mW/lm] | CAF (Circadian action factor) | EML | Circadian Light (CLA) [Circadian lux] | Circadian Stimulus (CS) | Rf | Rg | BLH | Energy in 440 < λ ≤ 490 nm/total energy 380 < λ ≤ 780 nm |
|---|---|---|---|---|---|---|---|---|---|---|---|
| 2400K Ch1 | 0.0463 | 0.0074 | 77.736 | 0.2481 | 0.30848 | 575 | 0.440 | 51 | 97 | 0.10961 | 1.04% |
| 2400K Ch2 | 0.0294 | 0.0047 | 75.434 | 0.2661 | 0.34238 | 631 | 0.457 | 56 | 109 | 0.06700 | 0.99% |
| 2400K Ch3 | 0.0442 | 0.0065 | 69.309 | 0.2453 | 0.28563 | 540 | 0.429 | 51 | 103 | 0.10573 | 0.92% |
| 1800K Ch1 | 0.0265 | 0.0032 | 26.837 | 0.1209 | 0.21275 | 374 | 0.360 | 77 | 103 | 0.02570 | 0.98% |
| 4000K Ch1 | 0.0725 | 0.0241 | 174.436 | 0.5949 | 0.79451 | 767 | 0.490 | 91 | 102 | 0.20390 | 15.87% |
| 4000K Ch2 | 0.1042 | 0.0367 | 178.778 | 0.6494 | 0.88924 | 875 | 0.511 | 85 | 96 | 0.28816 | 15.97% |
| 4000K Ch3 | 0.0930 | 0.0331 | 184.994 | 0.6516 | 0.89470 | 896 | 0.514 | 80 | 91 | 0.25199 | 18.10% |
| 4000K Ch4 | 0.0847 | 0.0307 | 188.638 | 0.6729 | 0.94619 | 938 | 0.521 | 74 | 87 | 0.22073 | 18.56% |
| 5000K Ch1 | 0.0916 | 0.0355 | 215.982 | 0.8368 | 1.10190 | 1325 | 0.567 | 81 | 97 | 0.28801 | 21.00% |

TABLE 4

|  | 320 < λ ≤ 400 | 400 < λ ≤ 500 | 500 < λ ≤ 600 | 600 < λ ≤ 700 | 700 < λ ≤ 780 |
|---|---|---|---|---|---|
| 2400K Ch3 | 9.92 | 44.53 | 83.33 | 100.00 | 7.55 |
| 2400K Ch2 | 8.59 | 39.69 | 75.82 | 100.00 | 3.09 |
| 2400K Ch1 | 11.11 | 51.02 | 105.53 | 100.00 | 4.41 |
| 1800K Ch1 | 7.61 | 4.42 | 39.66 | 100.00 | 11.52 |
| Exemplary 2$^{nd}$ channels min | 7.61 | 4.42 | 39.66 | 100.00 | 3.09 |
| Exemplary 2$^{nd}$ channels avg | 9.31 | 34.92 | 76.09 | 100.00 | 6.64 |
| Exemplary 2$^{nd}$ channels max | 11.11 | 51.02 | 105.53 | 100.00 | 11.52 |

TABLE 5

|  | 320 < λ ≤ 400 | 400 < λ ≤ 500 | 500 < λ ≤ 600 | 600 < λ ≤ 700 | 700 < λ ≤ 780 |
|---|---|---|---|---|---|
| 4000K Ch4 | 0.29 | 67.46 | 100.00 | 96.08 | 9.60 |
| 4000K Ch2 | 0.43 | 62.49 | 100.00 | 99.55 | 12.19 |
| 4000K Ch3 | 0.24 | 64.82 | 100.00 | 93.88 | 9.61 |
| 5000K Ch1 | 0.05 | 84.60 | 100.00 | 99.73 | 10.20 |
| Exemplary 1$^{st}$ channels min | 0.05 | 62.49 | 100.00 | 93.88 | 9.60 |
| Exemplary 1$^{st}$ channels avg | 0.25 | 69.84 | 100.00 | 97.31 | 10.40 |
| Exemplary 1$^{st}$ channels max | 0.43 | 84.60 | 100.00 | 99.73 | 12.19 |

TABLE 6

|  | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| 2400K Ch3 | 0.87 | 75.85 | 20.20 | 2.50 | 36.53 | 75.23 | 99.16 | 100.00 | 23.78 | 10.04 | 3.74 |
| 2400K Ch2 | 0.61 | 53.09 | 14.11 | 3.40 | 35.58 | 51.81 | 62.20 | 100.00 | 9.75 | 3.44 | 1.12 |
| 2400K Ch1 | 1.37 | 120.36 | 31.99 | 6.89 | 72.41 | 110.44 | 227.23 | 100.00 | 21.24 | 7.89 | 3.50 |
| 1800K Ch1 | 1.23 | 16.50 | 4.14 | 1.92 | 16.29 | 33.63 | 66.28 | 100.00 | 60.07 | 17.91 | 4.88 |
| Exemplary 2$^{nd}$ channels min | 0.61 | 16.50 | 4.14 | 1.92 | 16.29 | 33.63 | 62.20 | 100.00 | 9.75 | 3.44 | 1.12 |
| Exemplary 2$^{nd}$ channels avg | 1.02 | 66.45 | 17.61 | 3.68 | 40.20 | 67.78 | 113.72 | 100.00 | 28.71 | 9.82 | 3.31 |
| Exemplary 2$^{nd}$ channels max | 1.37 | 120.36 | 31.99 | 6.89 | 72.41 | 110.44 | 227.23 | 100.00 | 60.07 | 17.91 | 4.88 |

TABLE 7

|  | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| 4000K Ch4 | 0.39 | 0.59 | 30.88 | 98.73 | 67.12 | 76.66 | 100.00 | 84.15 | 50.00 | 13.89 | 4.63 |
| 4000K Ch2 | 0.54 | 1.99 | 44.28 | 79.86 | 78.17 | 75.94 | 100.00 | 95.38 | 52.20 | 18.93 | 5.61 |
| 4000K Ch3 | 0.29 | 0.70 | 37.77 | 87.23 | 65.19 | 79.15 | 100.00 | 82.62 | 48.47 | 13.93 | 4.68 |
| 5000K Ch1 | 0.01 | 1.49 | 66.19 | 129.05 | 96.22 | 88.49 | 100.00 | 115.83 | 63.66 | 18.66 | 5.03 |
| Exemplary 1$^{st}$ channels min | 0.01 | 0.59 | 30.88 | 79.86 | 65.19 | 75.94 | 100.00 | 82.62 | 48.47 | 13.89 | 4.63 |
| Exemplary 1$^{st}$ channels avg | 0.31 | 1.19 | 44.78 | 98.72 | 76.68 | 80.06 | 100.00 | 94.49 | 53.58 | 16.35 | 4.99 |
| Exemplary 1$^{st}$ channels max | 0.54 | 1.99 | 66.19 | 129.05 | 96.22 | 88.49 | 100.00 | 115.83 | 63.66 | 18.93 | 5.61 |

TABLE 8

|  | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| 2400K Ch3 | 0.00 | 0.02 | 1.13 | 22.91 | 77.86 | 23.21 | 3.62 | 0.62 | 2.70 | 13.97 | 34.57 | 48.20 |
| 2400K Ch2 | 0.00 | 0.02 | 0.72 | 14.60 | 49.67 | 14.79 | 2.29 | 0.48 | 3.64 | 15.31 | 27.77 | 31.81 |
| 2400K Ch1 | 0.00 | 0.04 | 1.83 | 37.29 | 126.84 | 37.77 | 5.84 | 1.20 | 8.20 | 35.22 | 63.53 | 73.06 |
| 1800K Ch1 | 0.00 | 0.00 | 2.61 | 29.27 | 5.68 | 4.41 | 4.36 | 1.12 | 2.94 | 11.91 | 22.59 | 30.12 |
| Exemplary 2$^{nd}$ channels min | 0.00 | 0.00 | 0.72 | 14.60 | 5.68 | 4.41 | 2.29 | 0.48 | 2.70 | 11.91 | 22.59 | 30.12 |

TABLE 8-continued

| | | | | | | | | | | | |
|---|---|---|---|---|---|---|---|---|---|---|---|
| Exemplary 2nd channels avg | 0.00 | 0.02 | 1.57 | 26.02 | 65.01 | 20.05 | 4.03 | 0.86 | 4.37 | 19.10 | 37.11 | 45.80 |
| Exemplary 2nd channels max | 0.00 | 0.04 | 2.61 | 37.29 | 126.84 | 37.77 | 5.84 | 1.20 | 8.20 | 35.22 | 63.53 | 73.06 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| 2400K Ch3 | 51.74 | 53.62 | 78.10 | 100.00 | 32.85 | 18.99 | 12.60 | 8.19 | 5.15 | 3.09 | 1.87 | 0.00 |
| 2400K Ch2 | 30.90 | 29.60 | 45.70 | 100.00 | 21.06 | 7.47 | 4.33 | 2.66 | 1.50 | 0.86 | 0.50 | 0.00 |
| 2400K Ch1 | 77.56 | 122.68 | 187.19 | 100.00 | 36.37 | 18.26 | 10.70 | 6.70 | 4.06 | 2.73 | 2.05 | 0.00 |
| 1800K Ch1 | 41.10 | 60.43 | 79.94 | 100.00 | 111.79 | 80.54 | 46.67 | 24.94 | 12.99 | 6.82 | 3.52 | 0.00 |
| Exemplary 2nd channels min | 30.90 | 29.60 | 45.70 | 100.00 | 21.06 | 7.47 | 4.33 | 2.66 | 1.50 | 0.86 | 0.50 | 0.00 |
| Exemplary 2nd channels avg | 50.33 | 66.58 | 97.73 | 100.00 | 50.52 | 31.32 | 18.58 | 10.62 | 5.93 | 3.38 | 1.99 | 0.00 |
| Exemplary 2nd channels max | 77.56 | 122.68 | 187.19 | 100.00 | 111.79 | 80.54 | 46.67 | 24.94 | 12.99 | 6.82 | 3.52 | 0.00 |

TABLE 9

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| 4000K Ch4 | 0.00 | 0.27 | 0.38 | 0.30 | 0.69 | 5.32 | 46.45 | 65.52 | 100.00 | 61.95 | 50.58 | 58.48 |
| 4000K Ch2 | 0.00 | 0.42 | 0.66 | 0.65 | 3.29 | 22.60 | 65.24 | 58.44 | 100.00 | 82.69 | 72.40 | 71.27 |
| 4000K Ch3 | 0.00 | 0.21 | 0.33 | 0.33 | 0.98 | 10.07 | 60.41 | 62.79 | 100.00 | 64.55 | 57.10 | 67.65 |
| 5000K Ch1 | 0.00 | 0.00 | 0.01 | 0.14 | 1.81 | 22.85 | 63.41 | 68.18 | 100.00 | 67.44 | 57.95 | 57.60 |
| Exemplary 1st channels min | 0.00 | 0.00 | 0.01 | 0.14 | 0.69 | 5.32 | 46.45 | 58.44 | 100.00 | 61.95 | 50.58 | 57.60 |
| Exemplary 1st channels avg | 0.00 | 0.23 | 0.34 | 0.35 | 1.69 | 15.21 | 58.88 | 63.73 | 100.00 | 69.16 | 59.51 | 63.75 |
| Exemplary 1st channels max | 0.00 | 0.42 | 0.66 | 0.65 | 3.29 | 22.85 | 65.24 | 68.18 | 100.00 | 82.69 | 72.40 | 71.27 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| 4000K Ch4 | 70.03 | 82.09 | 85.56 | 75.93 | 65.14 | 58.42 | 25.41 | 14.66 | 8.62 | 4.90 | 2.85 | 0.00 |
| 4000K Ch2 | 79.40 | 93.63 | 104.78 | 102.56 | 86.67 | 63.02 | 40.55 | 23.98 | 13.58 | 7.34 | 3.79 | 0.00 |
| 4000K Ch3 | 80.05 | 92.00 | 94.61 | 83.41 | 70.77 | 62.40 | 28.04 | 16.34 | 9.66 | 5.52 | 3.22 | 0.00 |
| 5000K Ch1 | 57.72 | 62.16 | 68.16 | 75.24 | 75.70 | 52.76 | 30.19 | 15.99 | 8.33 | 4.35 | 2.21 | 0.00 |
| Exemplary 1st channels min | 57.72 | 62.16 | 68.16 | 75.24 | 65.14 | 52.76 | 25.41 | 14.66 | 8.33 | 4.35 | 2.21 | 0.00 |
| Exemplary 1st channels avg | 71.80 | 82.47 | 88.28 | 84.29 | 74.57 | 59.15 | 31.05 | 17.74 | 10.05 | 5.53 | 3.02 | 0.00 |
| Exemplary 1st channels max | 80.05 | 93.63 | 104.78 | 102.56 | 86.67 | 63.02 | 40.55 | 23.98 | 13.58 | 7.34 | 3.79 | 0.00 |

TABLE 10

| | 320 < λ ≤ 330 | 330 < λ ≤ 340 | 340 < λ ≤ 350 | 350 < λ ≤ 360 | 360 < λ ≤ 370 | 370 < λ ≤ 380 | 380 < λ ≤ 390 | 390 < λ ≤ 400 | 400 < λ ≤ 410 | 410 < λ ≤ 420 | 420 < λ ≤ 430 | 430 < λ ≤ 440 |
|---|---|---|---|---|---|---|---|---|---|---|---|---|
| 2400K Ch3 | 0.00 | 0.00 | 0.00 | 0.04 | 0.26 | 1.62 | 7.91 | 30.16 | 70.32 | 59.07 | 27.46 | 11.12 |
| 2400K Ch2 | 0.00 | 0.00 | 0.00 | 0.03 | 0.18 | 1.16 | 5.65 | 21.61 | 50.41 | 42.34 | 19.67 | 7.95 |
| 2400K Ch1 | 0.00 | 0.00 | 0.00 | 0.06 | 0.40 | 2.52 | 12.31 | 47.07 | 109.79 | 92.21 | 42.85 | 17.31 |
| 1800K Ch1 | 0.00 | 0.00 | 0.00 | 0.00 | 0.00 | 5.56 | 42.52 | 19.80 | 8.19 | 3.91 | 3.64 | 5.74 |
| Exemplary 2nd channels min | 0.00 | 0.00 | 0.00 | 0.00 | 0.00 | 1.16 | 5.65 | 19.80 | 8.19 | 3.91 | 3.64 | 5.74 |
| Exemplary 2nd channels avg | 0.00 | 0.00 | 0.00 | 0.03 | 0.21 | 2.71 | 17.09 | 29.66 | 59.67 | 49.38 | 23.40 | 10.53 |
| Exemplary 2nd channels max | 0.00 | 0.00 | 0.00 | 0.06 | 0.40 | 5.56 | 42.52 | 47.07 | 109.79 | 92.21 | 42.85 | 17.31 |

| | 440 < λ ≤ 450 | 450 < λ ≤ 460 | 460 < λ ≤ 470 | 470 < λ ≤ 480 | 480 < λ ≤ 490 | 490 < λ ≤ 500 | 500 < λ ≤ 510 | 510 < λ ≤ 520 | 520 < λ ≤ 530 | 530 < λ ≤ 540 | 540 < λ ≤ 550 | 550 < λ ≤ 560 |
|---|---|---|---|---|---|---|---|---|---|---|---|---|
| 2400K Ch3 | 4.33 | 1.69 | 0.71 | 0.33 | 1.29 | 3.19 | 7.91 | 15.30 | 24.51 | 32.93 | 38.51 | 41.59 |
| 2400K Ch2 | 3.08 | 1.19 | 0.48 | 0.42 | 1.82 | 4.97 | 10.78 | 17.80 | 24.02 | 27.83 | 29.59 | 29.81 |
| 2400K Ch1 | 6.72 | 2.59 | 1.05 | 0.86 | 3.52 | 9.54 | 21.15 | 34.93 | 46.87 | 54.30 | 57.64 | 58.70 |
| 1800K Ch1 | 6.09 | 3.19 | 1.41 | 0.98 | 1.87 | 4.39 | 9.47 | 15.90 | 21.83 | 26.26 | 30.08 | 34.05 |
| Exemplary 2nd channels min | 3.08 | 1.19 | 0.48 | 0.33 | 1.29 | 3.19 | 7.91 | 15.30 | 21.83 | 26.26 | 29.59 | 29.81 |

TABLE 10-continued

| | | | | | | | | | | | |
|---|---|---|---|---|---|---|---|---|---|---|---|
| Exemplary 2nd channels avg | 5.05 | 2.16 | 0.91 | 0.65 | 2.13 | 5.52 | 12.33 | 20.98 | 29.31 | 35.33 | 38.95 | 41.04 |
| Exemplary 2nd channels max | 6.72 | 3.19 | 1.41 | 0.98 | 3.52 | 9.54 | 21.15 | 34.93 | 46.87 | 54.30 | 57.64 | 58.70 |

| | 560 < λ ≤ 570 | 570 < λ ≤ 580 | 580 < λ ≤ 590 | 590 < λ ≤ 600 | 600 < λ ≤ 610 | 610 < λ ≤ 620 | 620 < λ ≤ 630 | 630 < λ ≤ 640 | 640 < λ ≤ 650 | 650 < λ ≤ 660 | 660 < λ ≤ 670 | 670 < λ ≤ 680 |
|---|---|---|---|---|---|---|---|---|---|---|---|---|
| 2400K Ch3 | 42.83 | 43.16 | 43.36 | 45.76 | 54.76 | 75.03 | 100.00 | 66.18 | 32.55 | 22.04 | 17.39 | 14.17 |
| 2400K Ch2 | 29.31 | 28.39 | 27.39 | 27.87 | 32.98 | 52.35 | 100.00 | 86.71 | 27.42 | 11.91 | 7.93 | 6.02 |
| 2400K Ch1 | 59.43 | 64.08 | 79.86 | 115.51 | 152.93 | 145.17 | 100.00 | 59.25 | 35.20 | 22.72 | 16.72 | 12.37 |
| 1800K Ch1 | 39.62 | 47.89 | 58.66 | 70.02 | 80.33 | 89.88 | 100.00 | 112.92 | 122.48 | 115.54 | 96.01 | 75.48 |
| Exemplary 2nd channels min | 29.31 | 28.39 | 27.39 | 27.87 | 32.98 | 52.35 | 100.00 | 59.25 | 27.42 | 11.91 | 7.93 | 6.02 |
| Exemplary 2nd channels avg | 42.80 | 45.88 | 52.32 | 64.79 | 80.25 | 90.61 | 100.00 | 81.26 | 54.41 | 43.05 | 34.51 | 27.01 |
| Exemplary 2nd channels max | 59.43 | 64.08 | 79.86 | 115.51 | 152.93 | 145.17 | 100.00 | 112.92 | 122.48 | 115.54 | 96.01 | 75.48 |

| | 680 < λ ≤ 690 | 690 < λ ≤ 700 | 700 < λ ≤ 710 | 710 < λ ≤ 720 | 720 < λ ≤ 730 | 730 < λ ≤ 740 | 740 < λ ≤ 750 | 750 < λ ≤ 760 | 760 < λ ≤ 770 | 770 < λ ≤ 780 | 780 < λ ≤ 790 | 790 < λ ≤ 800 |
|---|---|---|---|---|---|---|---|---|---|---|---|---|
| 2400K Ch3 | 11.56 | 9.37 | 7.53 | 6.08 | 4.81 | 3.75 | 2.94 | 2.20 | 1.81 | 1.30 | 0.00 | 0.00 |
| 2400K Ch2 | 4.55 | 3.54 | 2.81 | 2.16 | 1.65 | 1.15 | 0.87 | 0.74 | 0.57 | 0.37 | 0.00 | 0.00 |
| 2400K Ch1 | 9.41 | 7.63 | 5.86 | 4.81 | 3.55 | 2.92 | 2.37 | 1.97 | 2.06 | 1.20 | 0.00 | 0.00 |
| 1800K Ch1 | 57.09 | 42.29 | 30.76 | 22.34 | 16.16 | 11.50 | 8.40 | 6.13 | 4.49 | 3.01 | 0.00 | 0.00 |
| Exemplary 2nd channels min | 4.55 | 3.54 | 2.81 | 2.16 | 1.65 | 1.15 | 0.87 | 0.74 | 0.57 | 0.37 | 0.00 | 0.00 |
| Exemplary 2nd channels avg | 20.65 | 15.71 | 11.74 | 8.85 | 6.54 | 4.83 | 3.64 | 2.76 | 2.23 | 1.47 | 0.00 | 0.00 |
| Exemplary 2nd channels max | 57.09 | 42.29 | 30.76 | 22.34 | 16.16 | 11.50 | 8.40 | 6.13 | 4.49 | 3.01 | 0.00 | 0.00 |

TABLE 11

| | 320 < λ ≤ 330 | 330 < λ ≤ 340 | 340 < λ ≤ 350 | 350 < λ ≤ 360 | 360 < λ ≤ 370 | 370 < λ ≤ 380 | 380 < λ ≤ 390 | 390 < λ ≤ 400 | 400 < λ ≤ 410 | 410 < λ ≤ 420 | 420 < λ ≤ 430 | 430 < λ ≤ 440 |
|---|---|---|---|---|---|---|---|---|---|---|---|---|
| 4000K Ch4 | 0.00 | 0.00 | 0.05 | 0.48 | 0.41 | 0.33 | 0.28 | 0.31 | 0.46 | 0.90 | 2.35 | 8.04 |
| 4000K Ch2 | 0.00 | 0.00 | 0.08 | 0.78 | 0.70 | 0.63 | 0.60 | 0.71 | 1.61 | 5.09 | 13.75 | 32.22 |
| 4000K Ch3 | 0.00 | 0.00 | 0.04 | 0.37 | 0.34 | 0.30 | 0.29 | 0.35 | 0.58 | 1.35 | 4.22 | 15.53 |
| 5000K Ch1 | 0.00 | 0.00 | 0.00 | 0.00 | 0.00 | 0.02 | 0.17 | 0.15 | 0.35 | 1.50 | 6.59 | 25.07 |
| Exemplary 1st channels min | 0.00 | 0.00 | 0.00 | 0.00 | 0.00 | 0.02 | 0.17 | 0.15 | 0.35 | 0.90 | 2.35 | 8.04 |
| Exemplary 1st channels avg | 0.00 | 0.00 | 0.04 | 0.41 | 0.36 | 0.32 | 0.34 | 0.38 | 0.75 | 2.21 | 6.73 | 20.22 |
| Exemplary 1st channels max | 0.00 | 0.00 | 0.08 | 0.78 | 0.70 | 0.63 | 0.60 | 0.71 | 1.61 | 5.09 | 13.75 | 32.22 |

| | 440 < λ ≤ 450 | 450 < λ ≤ 460 | 460 < λ ≤ 470 | 470 < λ ≤ 480 | 480 < λ ≤ 490 | 490 < λ ≤ 500 | 500 < λ ≤ 510 | 510 < λ ≤ 520 | 520 < λ ≤ 530 | 530 < λ ≤ 540 | 540 < λ ≤ 550 | 550 < λ ≤ 560 |
|---|---|---|---|---|---|---|---|---|---|---|---|---|
| 4000K Ch4 | 29.43 | 61.23 | 58.55 | 69.32 | 100.00 | 95.19 | 68.51 | 52.40 | 48.14 | 50.59 | 54.63 | 59.52 |
| 4000K Ch2 | 63.32 | 69.39 | 51.86 | 67.01 | 100.00 | 103.41 | 88.51 | 79.68 | 74.88 | 72.39 | 71.61 | 73.35 |
| 4000K Ch3 | 49.12 | 69.39 | 55.36 | 67.81 | 100.00 | 96.18 | 70.57 | 56.06 | 53.84 | 58.18 | 63.52 | 69.19 |
| 5000K Ch1 | 83.73 | 95.32 | 87.91 | 118.29 | 100.00 | 89.11 | 79.33 | 76.46 | 75.98 | 76.69 | 76.73 | 75.98 |
| Exemplary 1st channels min | 29.43 | 61.23 | 51.86 | 67.01 | 100.00 | 89.11 | 68.51 | 52.40 | 48.14 | 50.59 | 54.63 | 59.52 |
| Exemplary 1st channels avg | 56.40 | 73.83 | 63.42 | 80.61 | 100.00 | 95.97 | 76.73 | 66.15 | 63.21 | 64.46 | 66.62 | 69.51 |
| Exemplary 1st channels max | 83.73 | 95.32 | 87.91 | 118.29 | 100.00 | 103.41 | 88.51 | 79.68 | 75.98 | 76.69 | 76.73 | 75.98 |

| | 560 < λ ≤ 570 | 570 < λ ≤ 580 | 580 < λ ≤ 590 | 590 < λ ≤ 600 | 600 < λ ≤ 610 | 610 < λ ≤ 620 | 620 < λ ≤ 630 | 630 < λ ≤ 640 | 640 < λ ≤ 650 | 650 < λ ≤ 660 | 660 < λ ≤ 670 | 670 < λ ≤ 680 |
|---|---|---|---|---|---|---|---|---|---|---|---|---|
| 4000K Ch4 | 65.20 | 71.49 | 77.71 | 82.52 | 84.37 | 82.62 | 77.44 | 70.77 | 64.70 | 62.44 | 66.81 | 47.21 |
| 4000K Ch2 | 77.63 | 83.86 | 91.48 | 98.97 | 105.06 | 108.06 | 106.77 | 101.86 | 93.61 | 82.68 | 70.31 | 57.88 |
| 4000K Ch3 | 75.29 | 81.76 | 87.93 | 92.55 | 94.00 | 91.61 | 85.60 | 78.02 | 71.00 | 67.84 | 71.44 | 50.98 |
| 5000K Ch1 | 74.89 | 75.31 | 77.41 | 79.89 | 82.43 | 84.24 | 87.47 | 94.30 | 100.45 | 94.12 | 77.38 | 60.02 |
| Exemplary 1st channels min | 65.20 | 71.49 | 77.41 | 79.89 | 82.43 | 82.62 | 77.44 | 70.77 | 64.70 | 62.44 | 66.81 | 47.21 |
| Exemplary 1st channels avg | 73.25 | 78.10 | 83.63 | 88.48 | 91.47 | 91.63 | 89.32 | 86.24 | 82.44 | 76.77 | 71.48 | 54.02 |
| Exemplary 1st channels max | 77.63 | 83.86 | 91.48 | 98.97 | 105.06 | 108.06 | 106.77 | 101.86 | 100.45 | 94.12 | 77.38 | 60.02 |

TABLE 11-continued

| | 680 < λ ≤ 690 | 690 < λ ≤ 700 | 700 < λ ≤ 710 | 710 < λ ≤ 720 | 720 < λ ≤ 730 | 730 < λ ≤ 740 | 740 < λ ≤ 750 | 750 < λ ≤ 760 | 760 < λ ≤ 770 | 770 < λ ≤ 780 | 780 < λ ≤ 790 | 790 < λ ≤ 800 |
|---|---|---|---|---|---|---|---|---|---|---|---|---|
| 4000K Ch4 | 28.56 | 21.04 | 16.09 | 12.52 | 9.54 | 7.29 | 5.50 | 4.07 | 3.17 | 2.40 | 0.00 | 0.00 |
| 4000K Ch2 | 46.42 | 36.07 | 27.73 | 21.05 | 15.78 | 11.85 | 8.63 | 6.29 | 4.50 | 3.21 | 0.00 | 0.00 |
| 4000K Ch3 | 31.57 | 23.45 | 18.00 | 14.05 | 10.74 | 8.22 | 6.22 | 4.61 | 3.61 | 2.72 | 0.00 | 0.00 |
| 5000K Ch1 | 45.22 | 33.23 | 24.15 | 17.38 | 12.51 | 8.98 | 6.52 | 4.67 | 3.43 | 2.24 | 0.00 | 0.00 |
| Exemplary 1$^{st}$ channels min | 28.56 | 21.04 | 16.09 | 12.52 | 9.54 | 7.29 | 5.50 | 4.07 | 3.17 | 2.24 | 0.00 | 0.00 |
| Exemplary 1$^{st}$ channels avg | 37.94 | 28.44 | 21.49 | 16.25 | 12.14 | 9.08 | 6.72 | 4.91 | 3.68 | 2.64 | 0.00 | 0.00 |
| Exemplary 1$^{st}$ channels max | 46.42 | 36.07 | 27.73 | 21.05 | 15.78 | 11.85 | 8.63 | 6.29 | 4.50 | 3.21 | 0.00 | 0.00 |

TABLE 12

| | 400 < λ ≤ 470 nm | 470 < λ ≤ 510 nm | 530 < λ ≤ 570 nm | 600 < λ ≤ 630 nm | 630 < λ ≤ 780 nm |
|---|---|---|---|---|---|
| 2400K Ch3 | 14.063 | 1.000 | 12.431 | 18.374 | 16.714 |
| 2400K Ch2 | 7.136 | 1.000 | 6.611 | 10.443 | 9.461 |
| 2400K Ch1 | 7.971 | 1.000 | 6.693 | 11.715 | 5.576 |
| 1800K Ch1 | 1.990 | 1.000 | 7.873 | 16.512 | 43.711 |
| Exemplary 2$^{nd}$ channels min | 1.990 | 1.000 | 6.611 | 10.443 | 5.576 |
| Exemplary 2$^{nd}$ channels avg | 7.790 | 1.000 | 8.402 | 14.261 | 18.866 |
| Exemplary 2$^{nd}$ channels max | 14.063 | 1.000 | 12.431 | 18.374 | 43.711 |
| 4000K Ch4 | 0.475 | 1.000 | 0.693 | 0.746 | 1.268 |
| 4000K Ch2 | 0.652 | 1.000 | 0.830 | 0.906 | 1.643 |
| 4000K Ch3 | 0.575 | 1.000 | 0.799 | 0.825 | 1.385 |
| 5000K Ch1 | 0.634 | 1.000 | 0.652 | 0.596 | 1.493 |
| Exemplary 1$^{st}$ channels min | 0.475 | 1.000 | 0.652 | 0.596 | 1.268 |
| Exemplary 1$^{st}$ channels avg | 0.584 | 1.000 | 0.744 | 0.769 | 1.447 |
| Exemplary 1$^{st}$ channels max | 0.652 | 1.000 | 0.830 | 0.906 | 1.643 |

TABLE 13

EML Slope vs. CCT (per 1000K) for Pairings of Exemplary First/Second Lighting Channels

| | 4000K Ch1 | 4000K Ch2 | 4000K Ch3 | 4000K Ch4 | 5000K Ch1 |
|---|---|---|---|---|---|
| 2400K Ch1 | 0.305 | 0.363 | 0.374 | 0.396 | 0.305 |
| 2400K Ch2 | 0.284 | 0.342 | 0.353 | 0.375 | 0.292 |
| 2400K Ch3 | 0.320 | 0.377 | 0.389 | 0.411 | 0.314 |
| 1800K Ch1 | 0.265 | 0.307 | 0.315 | 0.332 | 0.277 |

TABLE 14

EML Ratio of First Lighting Channel to Second Lighting Channel for Pairings of Exemplary First/Second Lighting Channels

| | 4000K Ch1 | 4000K Ch2 | 4000K Ch3 | 4000K Ch4 | 5000K Ch1 |
|---|---|---|---|---|---|
| 2400K Ch1 | 2.6 | 2.9 | 2.9 | 3.1 | 3.6 |
| 2400K Ch2 | 2.3 | 2.6 | 2.6 | 2.8 | 3.2 |
| 2400K Ch3 | 2.8 | 3.1 | 3.1 | 3.3 | 3.9 |
| 1800K Ch1 | 3.7 | 4.2 | 4.2 | 4.4 | 5.2 |

TABLE 15

% Spectral Energy in Wavelength Range vs. Total Energy 320 nm to 800 nm

| | 400 < λ ≤ 410 | 410 < λ ≤ 420 | 420 < λ ≤ 430 | 430 < λ ≤ 440 | 440 < λ ≤ 450 | 450 < λ ≤ 460 | 460 < λ ≤ 470 | 470 < λ ≤ 480 | 480 < λ ≤ 490 | 490 < λ ≤ 500 | 500 < λ ≤ 510 | 510 < λ ≤ 520 |
|---|---|---|---|---|---|---|---|---|---|---|---|---|
| 2400K Ch3 | 7.11 | 5.97 | 2.78 | 1.12 | 0.44 | 0.17 | 0.071 | 0.033 | 0.13 | 0.32 | 0.80 | 1.55 |
| 2400K Ch2 | 6.65 | 5.59 | 2.60 | 1.05 | 0.41 | 0.16 | 0.064 | 0.056 | 0.24 | 0.66 | 1.42 | 2.35 |
| 2400K Ch1 | 7.19 | 6.04 | 2.81 | 1.13 | 0.44 | 0.17 | 0.069 | 0.056 | 0.23 | 0.62 | 1.38 | 2.29 |
| 1800K Ch1 | 0.56 | 0.27 | 0.25 | 0.39 | 0.42 | 0.22 | 0.097 | 0.067 | 0.13 | 0.30 | 0.65 | 1.09 |
| Exemplary 2$^{nd}$ channels min | 0.56 | 0.27 | 0.25 | 0.39 | 0.41 | 0.16 | 0.064 | 0.033 | 0.13 | 0.30 | 0.65 | 1.09 |
| Exemplary 2$^{nd}$ channels avg | 5.38 | 4.47 | 2.11 | 0.93 | 0.43 | 0.18 | 0.075 | 0.053 | 0.18 | 0.48 | 1.06 | 1.82 |
| Exemplary 2$^{nd}$ channels max | 7.19 | 6.04 | 2.81 | 1.13 | 0.44 | 0.22 | 0.097 | 0.067 | 0.24 | 0.66 | 1.42 | 2.35 |
| 4000K Ch4 | 0.03 | 0.05 | 0.14 | 0.47 | 1.71 | 3.55 | 3.40 | 4.02 | 5.80 | 5.52 | 3.97 | 3.04 |
| 4000K Ch2 | 0.07 | 0.23 | 0.62 | 1.44 | 2.84 | 3.11 | 2.32 | 3.00 | 4.48 | 4.63 | 3.97 | 3.57 |
| 4000K Ch3 | 0.03 | 0.07 | 0.22 | 0.82 | 2.58 | 3.64 | 2.91 | 3.56 | 5.25 | 5.05 | 3.71 | 2.94 |

TABLE 15-continued

% Spectral Energy in Wavelength Range vs. Total Energy 320 nm to 800 nm

| | 400 < λ ≤ 410 | 410 < λ ≤ 420 | 420 < λ ≤ 430 | 430 < λ ≤ 440 | 440 < λ ≤ 450 | 450 < λ ≤ 460 | 460 < λ ≤ 470 | 470 < λ ≤ 480 | 480 < λ ≤ 490 | 490 < λ ≤ 500 | 500 < λ ≤ 510 | 510 < λ ≤ 520 |
|---|---|---|---|---|---|---|---|---|---|---|---|---|
| 5000K Ch1 | 0.02 | 0.07 | 0.30 | 1.13 | 3.78 | 4.30 | 3.97 | 5.34 | 4.51 | 4.02 | 3.58 | 3.45 |
| Exemplary 1st channels min | 0.02 | 0.05 | 0.14 | 0.47 | 1.71 | 3.11 | 2.32 | 3.00 | 4.48 | 4.02 | 3.58 | 2.94 |
| Exemplary 1st channels avg | 0.04 | 0.10 | 0.32 | 0.96 | 2.73 | 3.65 | 3.15 | 3.98 | 5.01 | 4.81 | 3.81 | 3.25 |
| Exemplary 1st channels max | 0.07 | 0.23 | 0.62 | 1.44 | 3.78 | 4.30 | 3.97 | 5.34 | 5.80 | 5.52 | 3.97 | 3.57 |

TABLE 16

| ANSI Nominal CCT Boundary | CCT | Tolerance | | | Center | Boundaries | | | |
|---|---|---|---|---|---|---|---|---|---|
| | | duv | dCCT | dduv | | 1 | 2 | 3 | 4 |
| 2200 | 2238 | −0.0942 | ±102 | ±5.3 | Cx | 0.5018 | 0.4838 | 0.5046 | 0.5262 | 0.5025 |
| | | | | | Cy | 0.4153 | 0.3977 | 0.4007 | 0.4381 | 0.4348 |
| 2500 | 2470 | −0.3065 | ±109 | ±5.7 | Cx | 0.4792 | 0.4593 | 0.4838 | 0.5025 | 0.4813 |
| | | | | | Cy | 0.4131 | 0.3944 | 0.3977 | 0.4348 | 0.4319 |
| 2700 | 2725 | −0.0837 | ±145 | ±6.0 | Cx | 0.4578 | 0.4813 | 0.4562 | 0.4373 | 0.4593 |
| | | | | | Cy | 0.4101 | 0.4319 | 0.4260 | 0.3893 | 0.3944 |
| 3000 | 3045 | −0.0773 | ±175 | ±6.0 | Cx | 0.4338 | 0.4562 | 0.4299 | 0.4147 | 0.4373 |
| | | | | | Cy | 0.403 | 0.4260 | 0.4165 | 0.3814 | 0.3893 |
| 3500 | 3464 | −0.0698 | ±245 | ±6.0 | Cx | 0.4073 | 0.4299 | 0.3996 | 0.3889 | 0.4147 |
| | | | | | Cy | 0.3917 | 0.4165 | 0.4015 | 0.369 | 0.3814 |
| 4000 | 3985 | 0.9845 | ±275 | ±6.0 | Cx | 0.3818 | 0.4006 | 0.3736 | 0.3670 | 0.3898 |
| | | | | | Cy | 0.3797 | 0.4044 | 0.3874 | 0.3578 | 0.3716 |
| 5000 | 5027 | 2.0112 | ±283 | ±6.0 | Cx | 0.3447 | 0.3551 | 0.3376 | 0.3366 | 0.3515 |
| | | | | | Cy | 0.3553 | 0.376 | 0.3616 | 0.3369 | 0.3487 |
| 5700 | 5666 | 2.0235 | ±355 | ±6.0 | Cx | 0.3287 | 0.3376 | 0.3207 | 0.3222 | 0.3366 |
| | | | | | Cy | 0.3417 | 0.3616 | 0.3462 | 0.3243 | 0.3369 |
| 6500 | 6532 | 2.9989 | ±510 | ±6.0 | Cx | 0.3123 | 0.3205 | 0.3028 | 0.3068 | 0.3221 |
| | | | | | Cy | 0.3282 | 0.3481 | 0.3304 | 0.3113 | 0.3261 |

TABLE 17

| Designator | Exemplary Material(s) | Density (g/mL) | Emission Peak (nm) | FWHM (nm) | Emission Peak Range (nm) | FWHM Range (nm) |
|---|---|---|---|---|---|---|
| Composition "A" | Luag: Cerium doped lutetium aluminum garnet ($Lu_3Al_5O_{12}$) | 6.73 | 535 | 95 | 530-540 | 90-100 |
| Composition "B" | Yag: Cerium doped yttrium aluminum garnet ($Y_3Al_5O_{12}$) | 4.7 | 550 | 110 | 545-555 | 105-115 |
| Composition "C" | a 650 nm-peak wavelength emission phosphor: Europium doped calcium aluminum silica nitride ($CaAlSiN_3$) | 3.1 | 650 | 90 | 645-655 | 85-95 |
| Composition "D" | a 525 nm-peak wavelength emission phosphor: GBAM:$BaMgAl_{10}O_{17}$:Eu | 3.1 | 525 | 60 | 520-530 | 55-65 |
| Composition "E" | a 630 nm-peak wavelength emission quantum dot: any semiconductor quantum dot material of appropriate size for desired emission wavelengths | 5.1 | 630 | 40 | 625-635 | 35-45 |
| Composition "F" | a 610 nm-peak wavelength emission quantum dot: any semiconductor quantum dot material of appropriate size for desired emission wavelengths | 5.1 | 610 | 40 | 605-615 | 35-45 |

Those of ordinary skill in the art will appreciate that a variety of materials can be used in the manufacturing of the components in the devices and systems disclosed herein. Any suitable structure and/or material can be used for the various features described herein, and a skilled artisan will be able to select an appropriate structures and materials based on various considerations, including the intended use of the systems disclosed herein, the intended arena within which they will be used, and the equipment and/or accessories with which they are intended to be used, among other considerations. Conventional polymeric, metal-polymer composites, ceramics, and metal materials are suitable for use in the various components. Materials hereinafter discovered and/or developed that are determined to be suitable for use in the features and elements described herein would also be considered acceptable.

When ranges are used herein for physical properties, such as molecular weight, or chemical properties, such as chemical formulae, all combinations, and subcombinations of ranges for specific exemplar therein are intended to be included.

The disclosures of each patent, patent application, and publication cited or described in this document are hereby incorporated herein by reference, in its entirety.

Those of ordinary skill in the art will appreciate that numerous changes and modifications can be made to the exemplars of the disclosure and that such changes and modifications can be made without departing from the spirit of the disclosure. It is, therefore, intended that the appended claims cover all such equivalent variations as fall within the true spirit and scope of the disclosure.

We claim:

1. A lighting system comprising:
    a first white lighting channel configured to produce a first white light having a first color point and a first spectral power distribution and exhibiting a first Equivalent Melanopic Lux (EML) value;
    a second white lighting channel configured to produce a second white light having a second color point and a second spectral power distribution and exhibiting a second Equivalent Melanopic Lux (EML) value wherein the second EML value is at least twice that of the first EML value; and
    a control system configured to independently change the intensity of each at least one of the first lighting channel and the second lighting channel;
    wherein the first white light and second white light combined together form a third white light having a third color point and a third spectral power distribution;
    wherein the control system is further configured to change the intensity of each of the first lighting channel and the second lighting channel to provide the third white light with the third color point at a plurality of points along a predefined path near the black body locus in the 1931 CIE Chromaticity Diagram between and including both the first color point and the second color point;
    wherein the first spectral power distribution has a first circadian-stimulating energy characteristic, the second spectral power distribution has a second circadian stimulating energy characteristic, and the third spectral power distribution has a third circadian-stimulating energy characteristic; wherein the third white light at each of the plurality of points along the predefined path has an Ra value greater than or equal to 80.

2. The lighting system as claimed in claim 1, wherein the first color point has a CCT between about 4000K and about 6500K.

3. The lighting system of claim 1, wherein the first color point has a CCT of about 4000K.

4. The lighting system of claim 1, wherein the second color point has a CCT between about 2700K and about 1800K.

5. The lighting system of claim 1, wherein the second color point has a CCT of about 2400K.

6. The lighting system of claim 1, wherein the first lighting channel comprises an LED having an emission with a first peak wavelength of between about 440 nm and about 510 nm.

7. The lighting system of claim 1, wherein the second lighting channel comprises an LED having an emission with a second peak wavelength of between about 380 nm and about 420 nm.

* * * * *